United States Patent
Shao et al.

(10) Patent No.: US 10,918,322 B2
(45) Date of Patent: Feb. 16, 2021

(54) LIGHT RESTRICTION DESIGNS IN OPTICAL SENSING APPLICATIONS HAVING SHARED WINDOWS

(71) Applicant: Apple Inc., Cupertino, CA (US)

(72) Inventors: Guocheng Shao, San Jose, CA (US); Mathieu Charbonneau-Lefort, San Jose, CA (US); Ueyn L. Block, Menlo Park, CA (US)

(73) Assignee: Apple Inc., Cupertino, CA (US)

( * ) Notice: Subject to any disclaimer, the term of this patent is extended or adjusted under 35 U.S.C. 154(b) by 390 days.

(21) Appl. No.: 15/874,614

(22) Filed: Jan. 18, 2018

(65) Prior Publication Data

US 2018/0228414 A1  Aug. 16, 2018

Related U.S. Application Data

(60) Provisional application No. 62/458,525, filed on Feb. 13, 2017.

(51) Int. Cl.
*A61B 5/1455* (2006.01)
*G01J 1/04* (2006.01)
(Continued)

(52) U.S. Cl.
CPC ...... *A61B 5/14552* (2013.01); *A61B 5/02427* (2013.01); *G01J 1/0411* (2013.01);
(Continued)

(58) Field of Classification Search
CPC . A61B 5/1455; A61B 5/14552; A61B 5/6887; A61B 5/6897; A61B 5/6898;
(Continued)

(56) References Cited

U.S. PATENT DOCUMENTS 5,483,261 A   1/1996  Yasutake
5,488,204 A   1/1996  Mead et al.
(Continued)

FOREIGN PATENT DOCUMENTS

CN   105380634    3/2016
JP   2000-163031 A  6/2000
(Continued)

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.
(Continued)

*Primary Examiner* — Eric F Winakur
(74) *Attorney, Agent, or Firm* — Brownstein Hyatt Farber Schreck, LLP

(57) ABSTRACT

This relates to an electronic device configured for optical sensing having shared windows and including light restriction designs. The light restriction designs can include one or more of optical layers, optical films, lenses, and window systems configured to reduce or eliminate crosstalk between optical components. A plurality of accepting sections and a plurality of blocking sections can be employed to selectively allow light having an angle of incidence within one or more acceptance viewing angles and block light with angles of incidence outside of the acceptance viewing angles. In some examples, the light restriction designs can include variations in optical and structural properties can allow the light restriction designs to have spatially varying acceptance angles. Variations in structural properties can include, but are not limited to, differences in widths, heights, and/or tilts of the accepting sections and/or blocking sections.

17 Claims, 27 Drawing Sheets

(51) Int. Cl.
    *A61B 5/024*    (2006.01)
    *G02B 3/08*    (2006.01)
    *G02B 5/22*    (2006.01)

(52) U.S. Cl.
    CPC .............. *G01J 1/0488* (2013.01); *G02B 3/08* (2013.01); *G02B 5/22* (2013.01); *A61B 2562/0233* (2013.01); *G02B 2207/123* (2013.01)

(58) Field of Classification Search
    CPC ....... G01J 1/0488; G01J 1/0411; G02B 6/005; G02B 6/0053
    See application file for complete search history.

(56) References Cited

U.S. PATENT DOCUMENTS

| | | | |
|---|---|---|---|
| 5,825,352 | A | 10/1998 | Bisset et al. |
| 5,835,079 | A | 11/1998 | Shieh |
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,594,079 | B1 | 7/2003 | Trott et al. |
| 6,690,387 | B2 | 2/2004 | Zimmerman et al. |
| 7,015,894 | B2 | 3/2006 | Morohoshi |
| 7,184,064 | B2 | 2/2007 | Zimmerman et al. |
| 7,663,607 | B2 | 2/2010 | Hotelling et al. |
| 8,148,671 | B2 | 4/2012 | Kurahashi |
| 8,479,122 | B2 | 7/2013 | Hotelling et al. |
| 9,349,035 | B1* | 5/2016 | Gerber ............... G06K 9/00013 |
| 9,400,213 | B2 | 7/2016 | Uematsu et al. |
| 9,454,261 | B2 | 9/2016 | Duparre et al. |
| 2006/0197753 | A1 | 9/2006 | Hotelling |
| 2006/0291243 | A1* | 12/2006 | Niioka ................. G02B 6/0053 362/607 |

FOREIGN PATENT DOCUMENTS

| | | |
|---|---|---|
| JP | 2002-342033 A | 11/2002 |
| WO | WO 14/188411 | 11/2014 |
| WO | WO-2018/148326 A2 | 8/2018 |

OTHER PUBLICATIONS

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

* cited by examiner

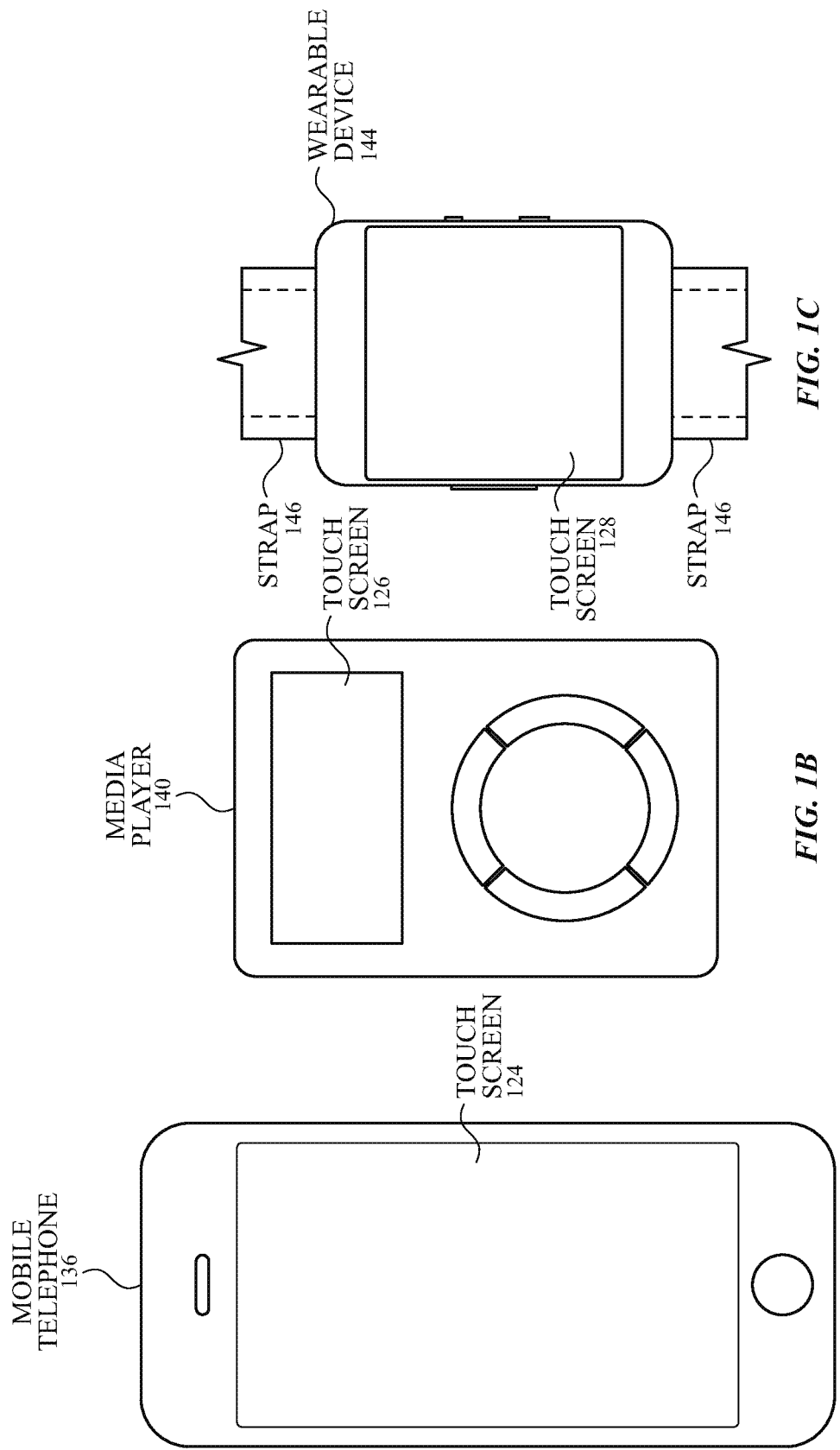

LIGHT RESTRICTION DESIGNS IN OPTICAL SENSING APPLICATIONS HAVING SHARED WINDOWS

CROSS-REFERENCE TO RELATED APPLICATIONS

This application claims the benefit of U.S. Provisional Patent Application No. 62/458,525 filed on Feb. 13, 2017, the entire disclosure of which is herein incorporated by reference for all purposes.

FIELD

This relates generally to a device configured for optical sensing having shared windows and including light restriction designs. More particularly, the disclosure relates to reduction or elimination of crosstalk between optical components for enhanced measurement accuracy and signal-to-noise ratio (SNR).

BACKGROUND

A user's physiological signals (e.g., pulse rate or arterial oxygen saturation) can be determined by pulse oximetry systems. In a basic form, pulse oximetry systems can utilize one or more point light sources (i.e., light with a defined beam size that exists an aperture 5 mm or less in diameter) to illuminate a user's tissue and one or more light detectors to receive light that enters and probes a subsurface volume of tissue. The light sources and light detectors can be in contact with the tissue or can be remote (i.e., not in contact) to the tissue surface.

SUMMARY

This relates to an electronic device configured for optical sensing having shared windows and including light restriction designs. The light restriction designs can include one or more of optical layers, optical films, lenses, and window systems configured to reduce or eliminate crosstalk between optical components. A plurality of accepting sections and a plurality of blocking sections can be employed to selectively allow light having an angle of incidence within one or more acceptance viewing angles and block light with angles of incidence outside of the acceptance viewing angles. In some examples, the light restriction designs can be vary in optical and structural properties. The variations in optical and structural properties can allow the light restriction designs to have spatially varying acceptance angles. For example, one location of an optical film can be allow light with an angle of incidence of a first acceptance angle to pass through (e.g., narrow acceptance viewing angles), whereas another location of the optical film may block light having the same angle of incidence (e.g., wide acceptance viewing angles). Variations in structural properties can include, but are not limited to, differences in widths, heights, and/or tilts of the accepting sections and/or blocking sections. In some examples, the optical film can be bi-directional accepting light incident from multiple directions, but configured with different ranges of acceptance angles for the different directions. Examples of the disclosure can include the optical layer including one or more of a Fresnel lens an infrared transparent material, and multiple types of accepting and/or blocking sections. Methods for manufacturing the optical layers, optical films, lenses, and window systems and operating the device are further disclosed.

BRIEF DESCRIPTION OF THE DRAWINGS

FIGS. 1A-1C illustrate systems in which examples of the disclosure can be implemented.

DETAILED DESCRIPTION

Figure 2A:
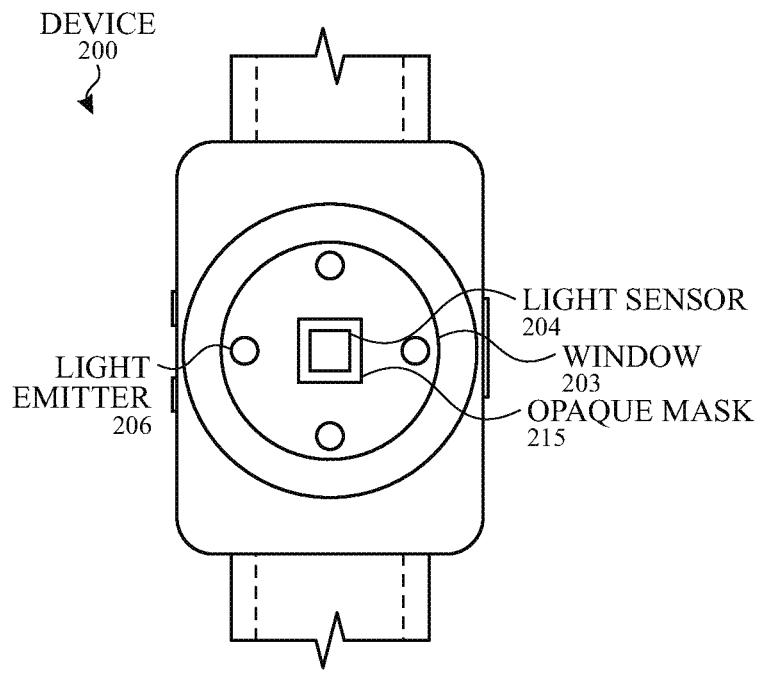
FIG. 2A illustrates a top view of an exemplary electronic device including light sensors and light emitters for measuring one or more physiological signals according to examples of the disclosure.

In the following description of examples, reference is made to the accompanying drawings in which it is shown by way of illustration specific examples that can be practiced. It is to be understood that other examples can be used and structural changes can be made without departing from the scope of the various examples. Numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

A user's physiological signals (e.g., pulse rate and arterial blood oxygen saturation) can be determined by measurements using pulse oximetry systems. Such pulse oximetry systems can be designed to be sensitive to changes in the red blood cell number, concentration, volume, or blood oxygen state included in the sample or a user's vasculature. In a basic form, pulse oximetry systems can employ a light source that injects light into the user's tissue and a light detector to receive light that reflects and/or scatters and exits the tissue. The light source(s) and light detector(s) can be in contact or can be remote to (i.e., not in contact with) the tissue. In some instances, some of the reflected and/or scattered light measured by the light sensor can be include light that has reflected off one or more interfaces of the device and/or one or more superficial layers of the user. In some instances, the unwanted light signal reflected off the one or more interfaces and/or superficial layers may lead to an erroneous signal, a low signal-to-noise ratio (SNR), or both.

This relates to an electronic device configured for optical sensing having shared windows and including light restriction designs. The light restriction designs can include one or more of optical layers, optical films, lenses, and window systems configured to reduce or eliminate crosstalk between optical components. A plurality of accepting sections and a plurality of blocking sections can be employed to selectively allow light having an angle of incidence within one or more acceptance viewing angles and block light with angles of incidence outside of the acceptance viewing angles. In some examples, the light restriction designs can be vary in optical and structural properties. The variations in optical and structural properties can allow the light restriction designs to have spatially varying acceptance angles. For example, one location of an optical film can be allow light with an angle of incidence of a first acceptance angle to pass through (e.g., narrow acceptance viewing angles), whereas another location of the optical film may block light having the same angle of incidence (e.g., wide acceptance viewing angles). Variations in structural properties can include, but are not limited to, differences in widths, heights, and/or tilts of the accepting sections and/or blocking sections. In some examples, the optical film can be bi-directional accepting light incident from multiple directions, but configured with different ranges of acceptance angles for the different directions. Examples of the disclosure can include the optical layer including one or more of a Fresnel lens an infrared transparent material, and multiple types of accepting and/or blocking sections. Methods for manufacturing the optical layers, optical films, lenses, and window systems and operating the device are further disclosed.

Representative applications of the apparatus and methods according to the present disclosure are described in this section. These examples are being provided solely to add context and aid in the understanding of the described examples. It will thus be apparent to one skilled in the art that the described examples may be practiced without some or all of the specific details. Other applications are possible, such that the following examples should not be taken as limiting.

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can be attached to a user using a strap 146. The systems of FIGS. 1A-1C can utilize the optical layers, optical films, lenses, window systems, and/or methods for detecting one or more physiological signals as will be disclosed.

Figure 2B:
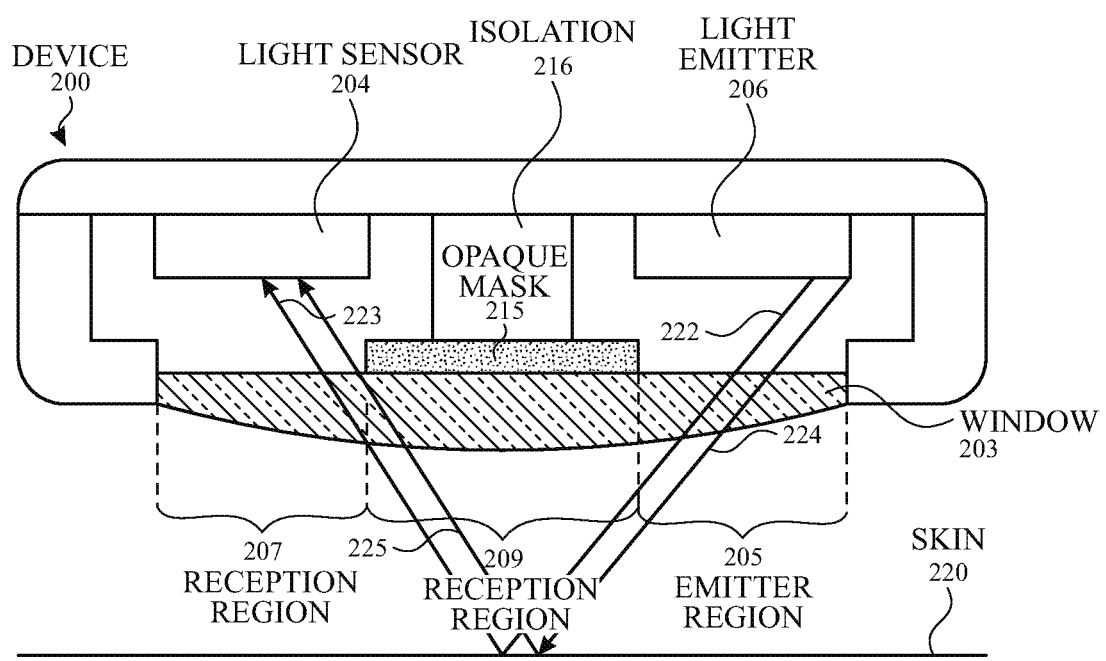
FIG. 2B illustrates a cross-sectional view of an exemplary electronic device including light sensors and light emitters for measuring one or more physiological signals according to examples of the disclosure.

FIG. 2A illustrates a top view and FIG. 2B illustrates a cross-sectional view of an exemplary electronic device including light sensors and light emitters for measuring one or more physiological signals according to examples of the disclosure. The top view in FIG. 2A can be viewed as the underside of wearable device 144 of FIG. 1C, for example. A light sensor 204 can be located proximate to a light emitter 206 on a surface (e.g., external surface of the housing opposite the touch screen) of device 200. In some examples, light sensor 204 and light emitter 206 can be located in the same cavity, which can be covered by window 203. Device 200 can be situated such that light sensor 204 and light emitter(s) 206 are proximate to a skin 220 of a user. For example, device 200 can be held in a user's hand or strapped to a user's wrist, among other possibilities.

Light emitter 206 can generate light 222 exiting window 203. Light 222 can be directed towards and incident upon the user's skin 220. A portion of light 222 can be absorbed by skin 220, vasculature, and/or blood, and a portion of light (i.e., light 223) can reflect back for detection by light sensor 204. Light 224 can also be incident upon skin 220, a portion of light 224 can be absorbed by skin 220, vasculature, and/or blood, and a portion of light (i.e., light 225) can reflect back towards device 200.

To prevent or reduce optical crosstalk between light sensor 204 and light emitter 206, device 200 can include isolation 216 located between light sensor 204 and light emitter 206. Isolation can divide the cavity into a plurality of sub-cavities. In some examples, the light sensors can be located in one or more sub-cavities separate from the light emitters, each sub-cavity can define regions of the window. For example, an emitter region 205 of a window can overlay a sub-cavity having an emitter, and a reception region 207 of a window can overlay a sub-cavity having a detector. The window can further include a boundary region 209 that overlays the isolation 216 and/or an opaque mask 215.

Opaque mask 215 can prevent isolation 216 from being visible to the human eye. In some examples, opaque mask 215 and isolation 216 can include the same materials and/or functions (e.g., act as an optical isolation and/or cosmetic layer). At least one end of opaque mask 215 and/or isolation 216 can located at or in close proximity to the internal surface (i.e., surface furthest from the exterior surface of the housing of device 200) of window 203.

Figure 2C:
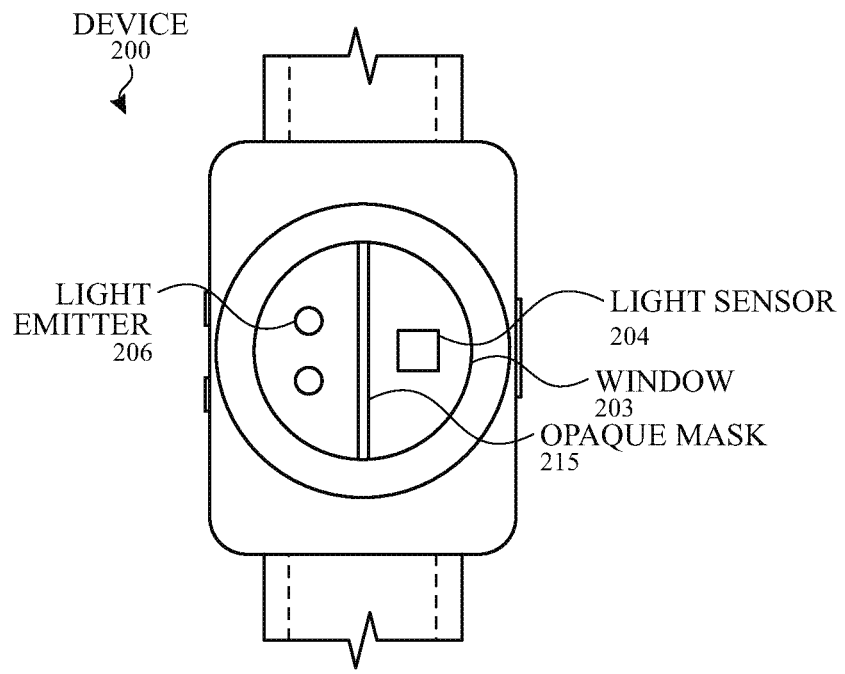
FIG. 2C illustrates a top view of an exemplary electronic device including an alternative configuration of light sensors and light emitters for measuring one or more physiological signals according to examples of the disclosure.

FIG. 2C illustrates a top view of an exemplary electronic device including an alternative configuration of light sensors and light emitters for measuring one or more physiological signals according to examples of the disclosure. Light emitters 206 may be located in one sub-cavity, and light sensor 204 may be located in another sub-cavity. The isolation (not shown) and opaque mask 215 be included in the boundary region of window 203. Although FIGS. 2A-2C illustrate a single window, examples of the disclosure can include a device including multiple windows and multiple cavities. Each window can include any type of configuration of light sensors and light emitters. The configuration of optical components in different cavities can be the same or may differ, as exemplified in FIG. 2E. For example, the device can include optical components in one cavity and window having the configuration illustrated in FIG. 2A and optical components in another cavity and window having the configuration illustrated in FIG. 2C.

Figure 2D:
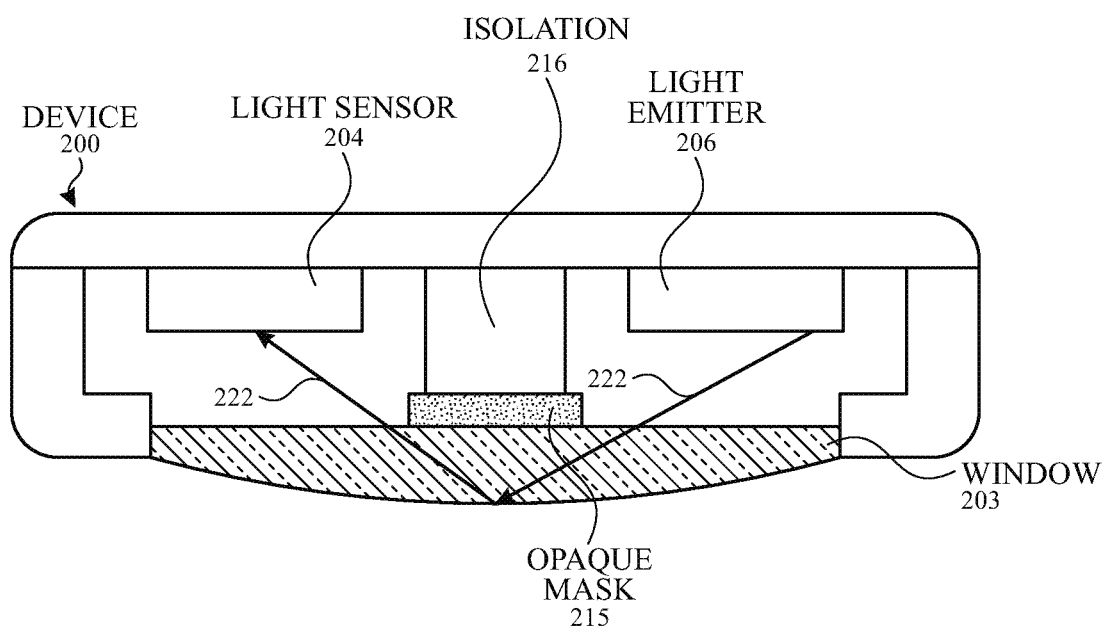
FIG. 2D illustrates a cross-sectional view of an exemplary electronic device including light sensors detecting one or more unwanted light rays according to examples of the disclosure.
Figure 2E:
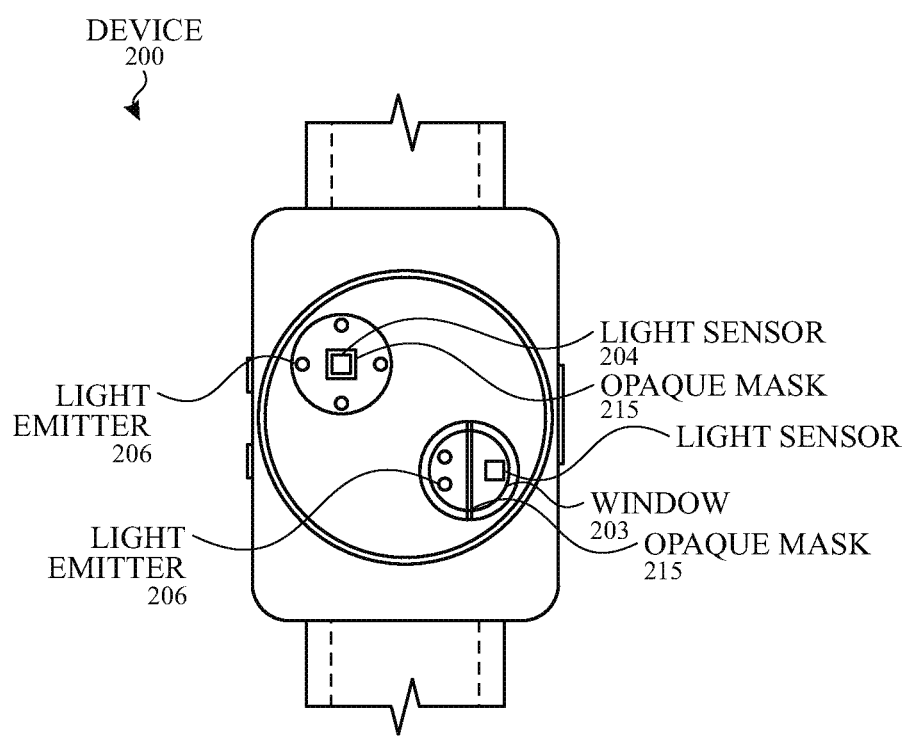
FIG. 2E illustrates a top view of an exemplary electronic device including an alternative configuration of light sensors and light emitters for measuring one or more physiological signals according to examples of the disclosure.

In some examples, light detected by the light sensor can include unwanted light, thereby introducing noise in the measurement signal. FIG. 2D illustrates a cross-sectional view of an exemplary electronic device including light sensors detecting one or more unwanted light rays according to examples of the disclosure. Unwanted light can include light emitted by light emitter 206 that has not penetrated to one or more intended layers in skin 220. For example, light 222 can be emitted by light emitter 206. Instead of exiting window 203, light 222 may reflect at one or more interfaces of window 203 (and/or material, such as residue or dirt, located on the window 203) due to reflecting at the interface(s) and/or total internal reflection. Light 222 may exit window 203 at some point, reaching light sensor 204. In this manner, light 222 may not have penetrated to skin 220 and thus, may not include any or little relevant physiological information. In some examples, light 222 detected by light sensor 204 can include the same information as light 222 emitted by light emitter 206.

Figure 3A:
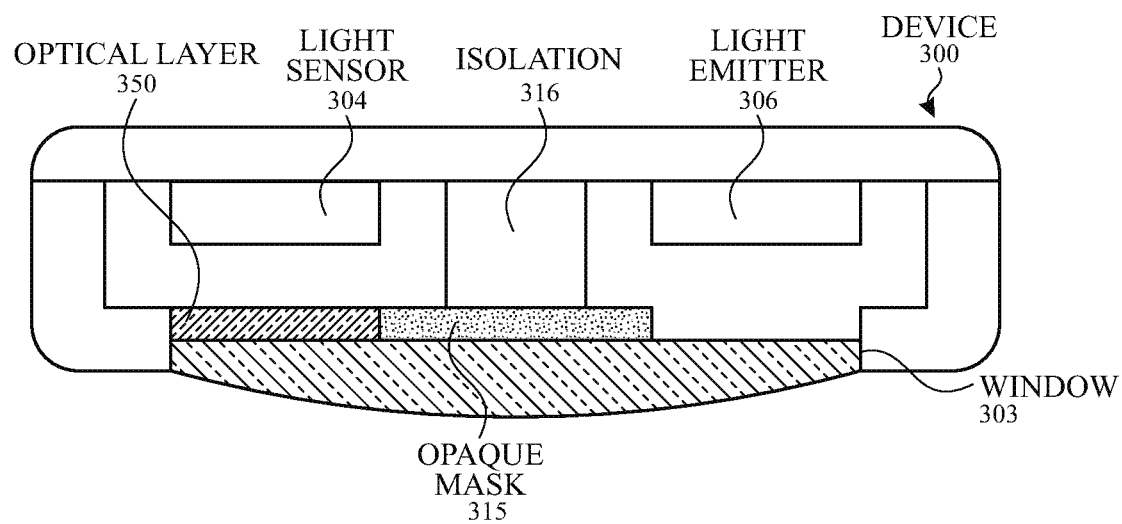
FIG. 3A illustrates a cross-sectional view of an exemplary device including an optical layer configured to selective control the angles of light that pass through the optical film to the light sensor according to examples of the disclosure.

Another way to overcome or prevent the light sensor from detecting unwanted light can be to selectively control the angle(s) of light that reach the light sensor. FIG. 3A illustrates a cross-sectional view of an exemplary device including an optical layer configured to selective control the angles of light that pass through the optical layer to the light sensor according to examples of the disclosure. Device 300 can include light sensor 304, light emitter 306, opaque mask 315, isolation 316, and window 303 each having one or more properties and/or functions as similar components discussed with respect to FIGS. 2A-2D. In some examples, window 303 can be shared among multiple optical components. For example, window 303 overlay both light sensor and light emitter cavities. Examples of the disclosure are not limited to window sharing among optical components of different types (e.g., a light emitter and light sensor pair). Device 300 can further include optical layer 350. Optical layer 350 can include an optical film, discussed in further detail blow, configured to selectively control the angle(s) of light that transmit through optical layer 350 to light sensor 304. For example, the optical film can include a plurality of accepting sections, as will be discussed below. Each accepting section can allow a set of acceptance viewing angles, such as ±30° relative to normal incidence (i.e., 60°-120° relative to the flat surface of the window), to pass through. Viewing angles outside of the acceptance viewing angles may not transmit through to light sensor 304 and may be blocked (e.g., absorbed or reflected back).

Figure 3B:
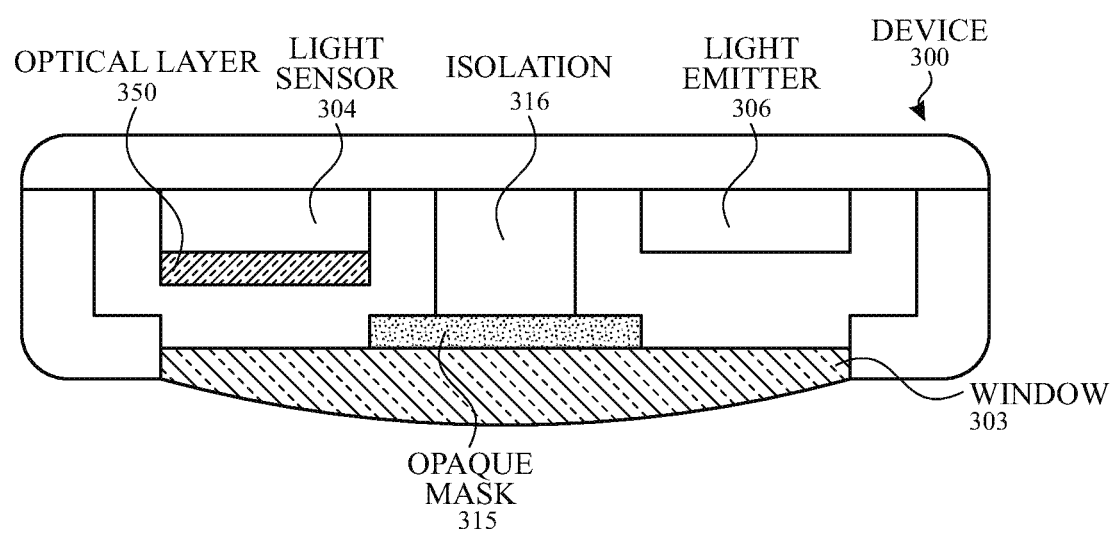
FIG. 3B illustrates a cross-sectional view of an exemplary device including an optical layer disposed on or located in close proximity to the light sensor according to examples of the disclosure.
Figure 3C:
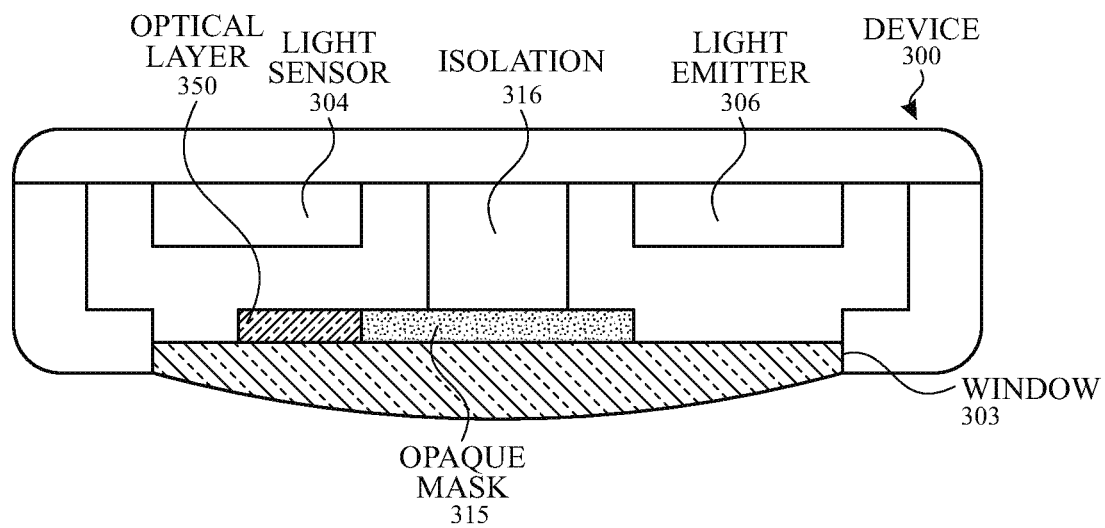
FIG. 3C illustrates a cross-sectional view of an exemplary device including an optical layer covering a portion of the reception region of a window according to examples of the disclosure.
Figure 4A:
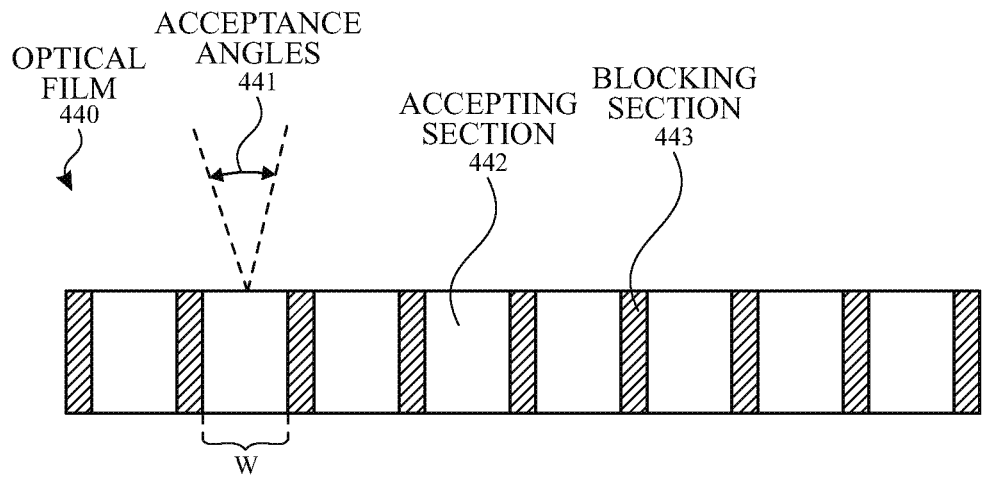
FIG. 4A illustrates a cross-sectional view of an exemplary optical layer according to examples of the disclosure.

Optical layer 350 can be placed at various locations. For example, as shown in FIG. 3A, optical layer 350 can be disposed on (e.g., contacting) or located in close proximity to the reception region of window 303. In some examples, the optical layer can be disposed on or located in close proximity to the light sensor, as illustrated in FIG. 3B. In some examples, the optical layer 350 may cover a portion of the reception region of the window, as illustrated in FIG. 3C. In some examples, a Fresnel lens can be disposed on the optical layer 350 (as illustrated in FIG. 4D and discussed below).

Figure 3D:
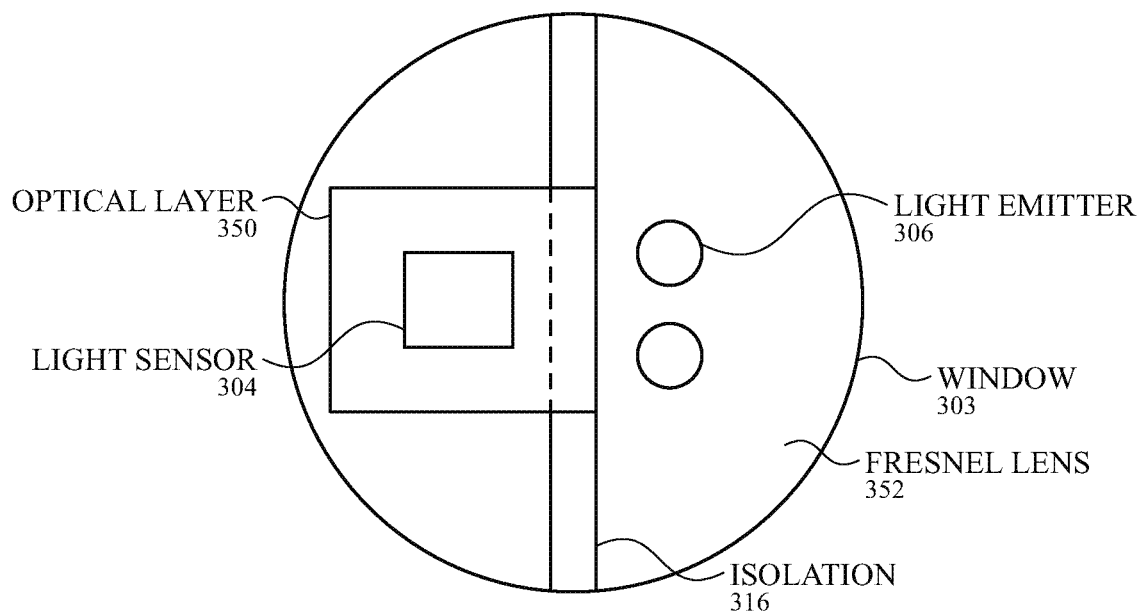
FIGS. 3D-3E illustrate cross-sectional and top views of an exemplary device including an optical layer integrated with a Fresnel lens, according to examples of the disclosure.
Figure 3E:
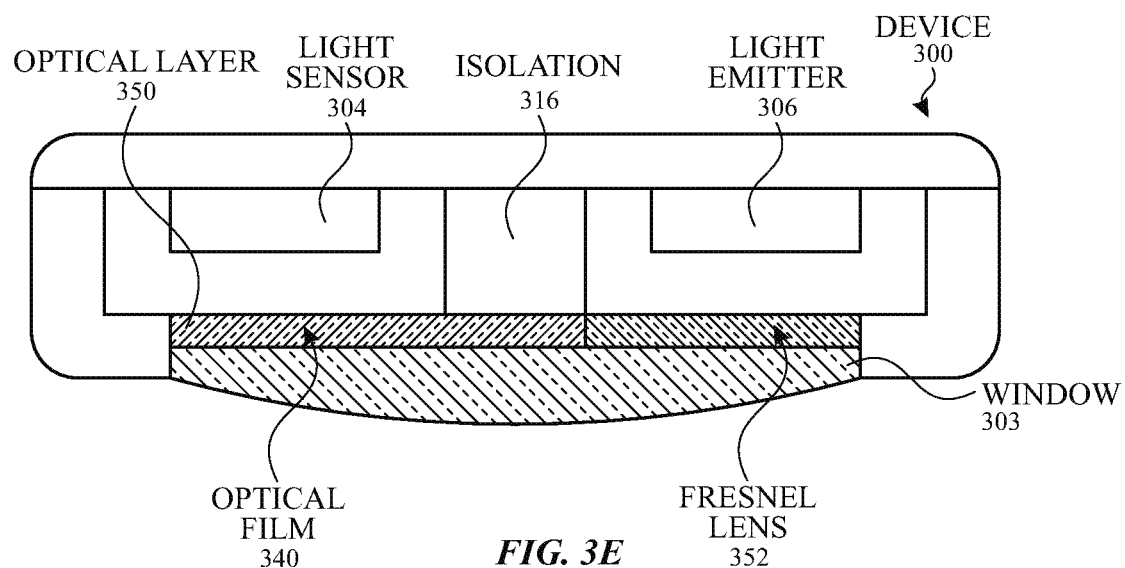

Examples of the disclosure can further include an optical layer including an optical film and a Fresnel lens, as illustrated in FIGS. 3D-3E. Optical layer 350 can include optical film 340 and Fresnel lens 352. Optical film 340 can be at least partially disposed or located in the reception region of window 303. Fresnel lens 352 can be disposed or located in close proximity to the emitter region of window 303. In some examples, optical film 340 can be disposed on light sensor 304, and Fresnel lens 352 can be disposed on light emitter 306. In some examples, optical film 340 can spatially extend beyond (e.g., outside the field of view of the optical component) the reception region of window 303 into the boundary region. That is, optical film 340 can be disposed on isolation 316 and/or the cavity including light sensor 304. Fresnel lens 352 can include, for example, clear epoxy. In some examples, the Fresnel lens 352 can be integrated with the optical film 340, thereby forming a single continuous layer that can be deposited in one processing step. For example, optical layer 350 (including optical film 340 and Fresnel lens 352) can be made from a continuous epoxy component. In other examples, optical layer 350 can be formed by adhering or depositing the optical film 340 to Fresnel lens 352.

Figure 3F:
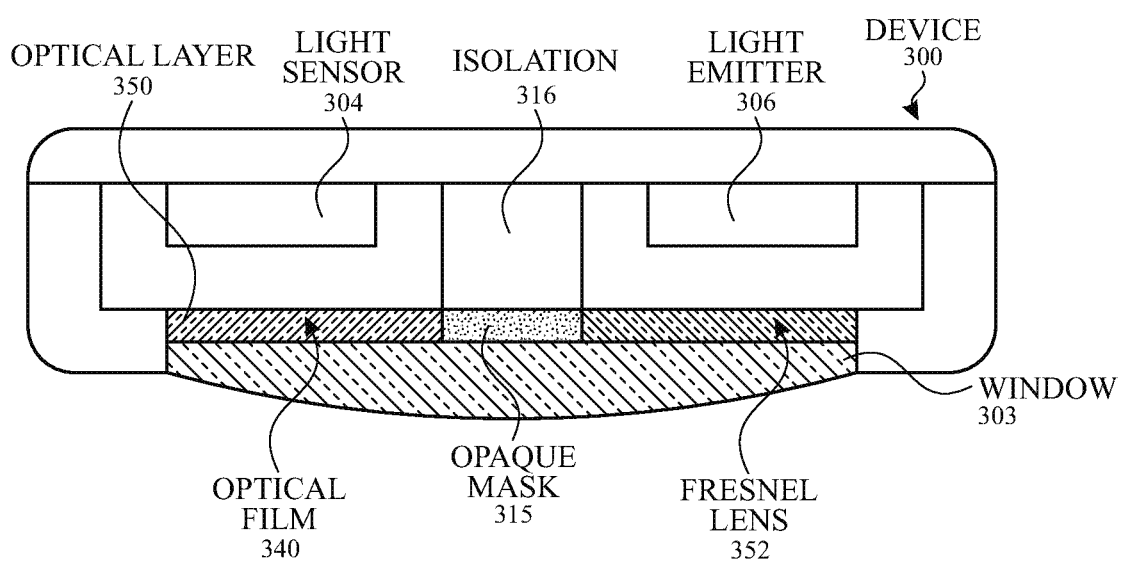
FIGS. 3F-3G illustrate cross-sectional views of exemplary devices including an optical layer and an opaque mask according to examples of the disclosure.
Figure 3G:
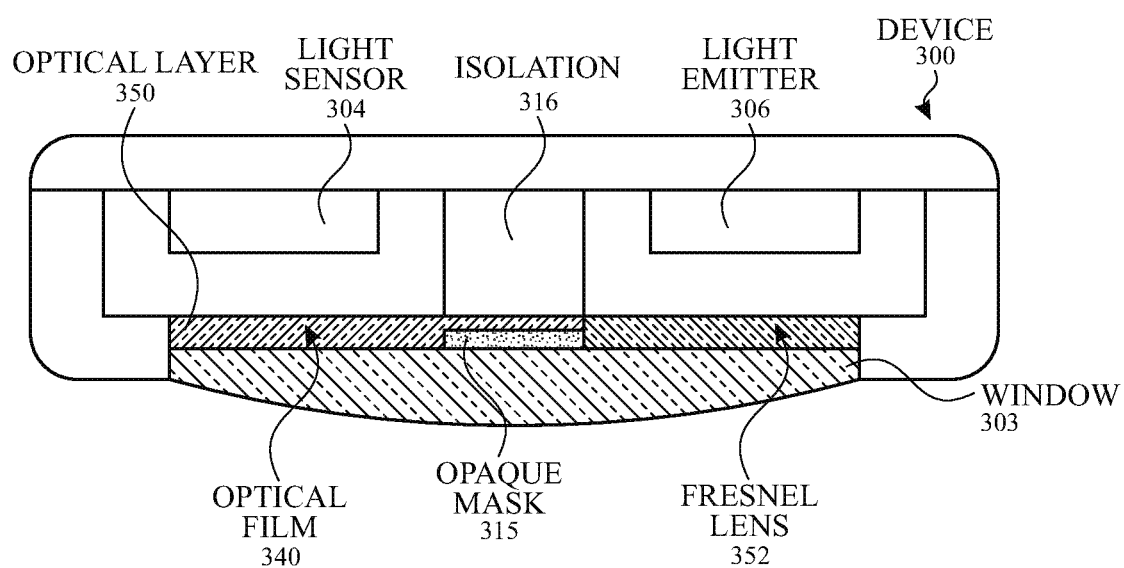

In some examples, optical layer 350 can include an opaque mask 315, as illustrated in FIG. 3F, which can be a continuous layer (e.g., formed in a single processing step). In some examples, device 300 can include an opaque mask 315 separate from, but disposed on (or in close proximity to), optical layer 350, as illustrated in FIG. 3G. Although the figures illustrate optical film 340, optical layer 350, and/or Fresnel lens 352 as contacting window 303, examples of the disclosure can include one or more layers, such as an adhesive layer, located between window 303 and one or more of the optical film 340, optical layer 350, and Fresnel lens 352. In some examples, the device can include a Fresnel lens disposed on or adhered to the optical film 340. In some examples, the device can include a Fresnel lens disposed on (or located in close proximity to) the light sensor 304 and the optical film 340 disposed on (or located in close proximity to) the window 303, or vice versa. The device can include, for example, multiple Fresnel lenses, at least one optically coupled to a light sensor, and at least one optically coupled to a light emitter.

The optical film 440 can be configured to accept one or more acceptance angles and block other angles. The optical film can have variations in both optical and structural properties. That is, one area of the optical film can have different optical and structural properties than another area. Exemplary varied structural properties relate to the widths of the accepting sections, the heights of the blocking sections, and the tilt of the blocking sections. FIG. 4A illustrates a cross-sectional view of an exemplary optical film according to examples of the disclosure. Optical film 440 can include a plurality of sections, such as accepting section 442 and blocking section 443. In some examples, optical film 440 can be located between a plurality of substrate layers (not shown), which can be configured to provide mechanical support to the plurality of sections. Some of the plurality of sections (e.g., accepting section 442) can be configured to allow light incident on optical film 440 having an angle of incidence within the acceptance angles 441 to pass through. Other of the plurality of sections (e.g., blocking section 443) can be configured to block light incident on optical film 440 having an angle of incidence outside the acceptance angles 441 from passing through optical film 440. In some examples, each accepting section 442 can include the same acceptance angles 441. Additionally, the spacing between adjacent sections 443 and/or width w of accepting sections 442 can be the same. In this manner, the number of layers and/or thickness of the optical layer and the device can be reduced. Accepting sections 442 can include clear epoxy, and blocking sections 443 can include opaque (e.g., black) epoxy, for example.

Figure 4B:
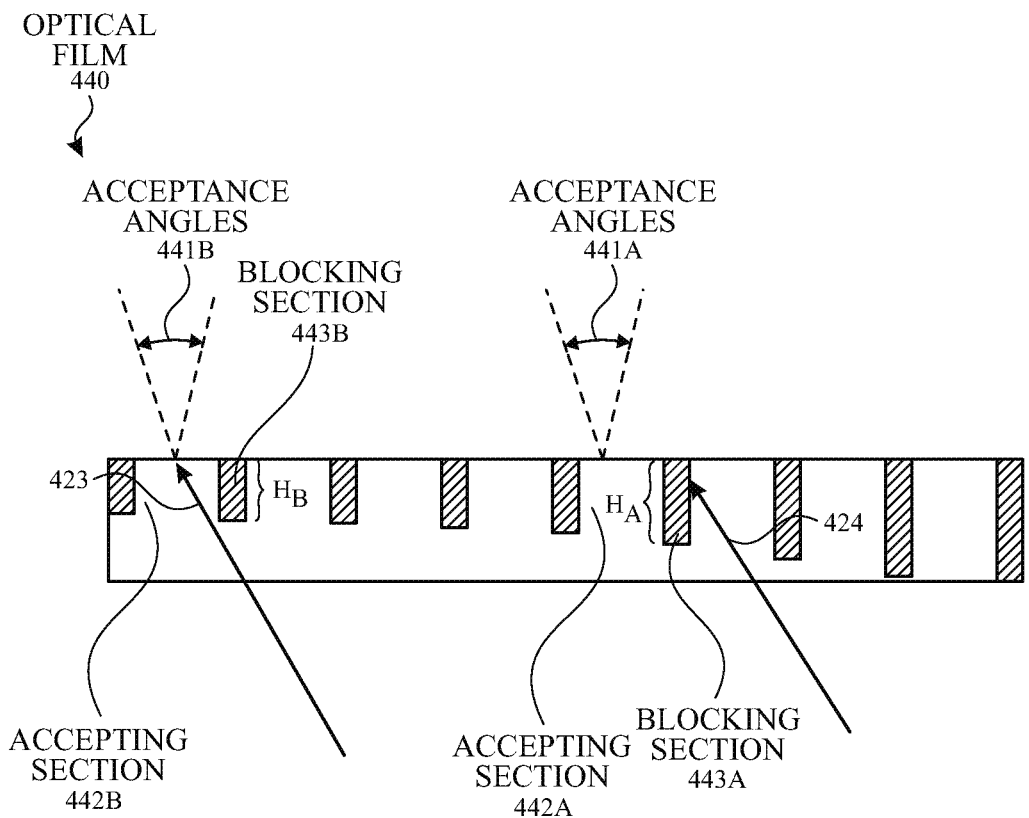
FIG. 4B illustrates a cross-sectional view of an exemplary optical layer including blocking sections of various heights according to examples of the disclosure.

In some examples, the height of the blocking sections can vary, as illustrated in FIG. 4B. For example, blocking section 443A can have a height $H_A$, and blocking section 443B can have a height $H_B$. Height $H_A$ can be different from height $H_B$. Due to the differences in height, corresponding accepting sections can be configured with different acceptance angles. For example, accepting section 442A corresponding to blocking section 443A can have narrower acceptance angles 441A than acceptance angles 441B, corresponding to accepting section 442B and blocking section 443B. Light 423 and light 424 can have the same angle of incidence. Due to height $H_A$ of blocking section 443A being greater than height $H_B$ of blocking section 443B, light 424 can be blocked, whereas light 423 can be accepted (i.e., allowed to pass through optical film 440). In some examples, blocking section 443A can be located closer to the light emitter (e.g., light emitter 306 illustrated in FIG. 3A) than blocking section 443B. In this manner, the acceptance viewing angles of the optical film 440 can be varied. In some examples, the heights of the blocking sections can vary gradually (e.g., each blocking section 443 can have a height less than an adjacent blocking section 443 and a height greater than the other adjacent blocking section 443). In some examples, the optical film can include a plurality of blocking sections 443 with the same height, and each plurality can different heights from other pluralities. Examples of the disclosure can include all of the blocking sections having the same height while one end of all of the blocking sections contact only one substrate layer (and not the other substrate layer).

Figure 4C:
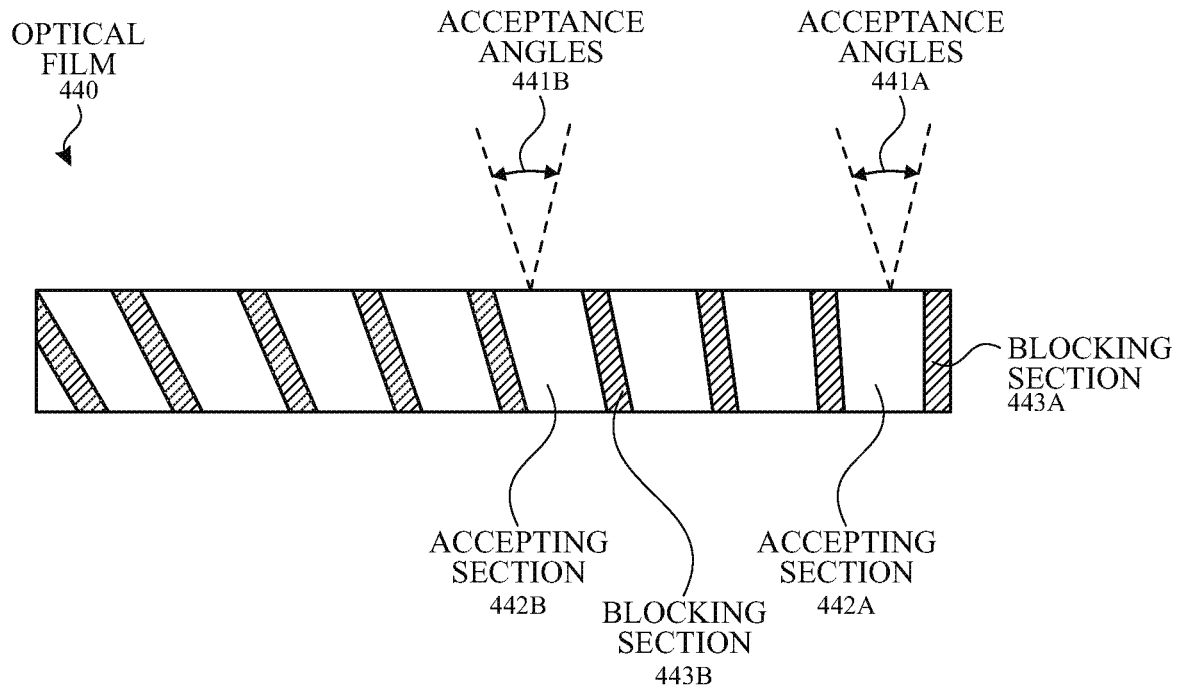
FIG. 4C illustrates a cross-sectional view of an exemplary optical layer including blocking sections of various tilt angles according to examples of the disclosure.
Figure 4D:
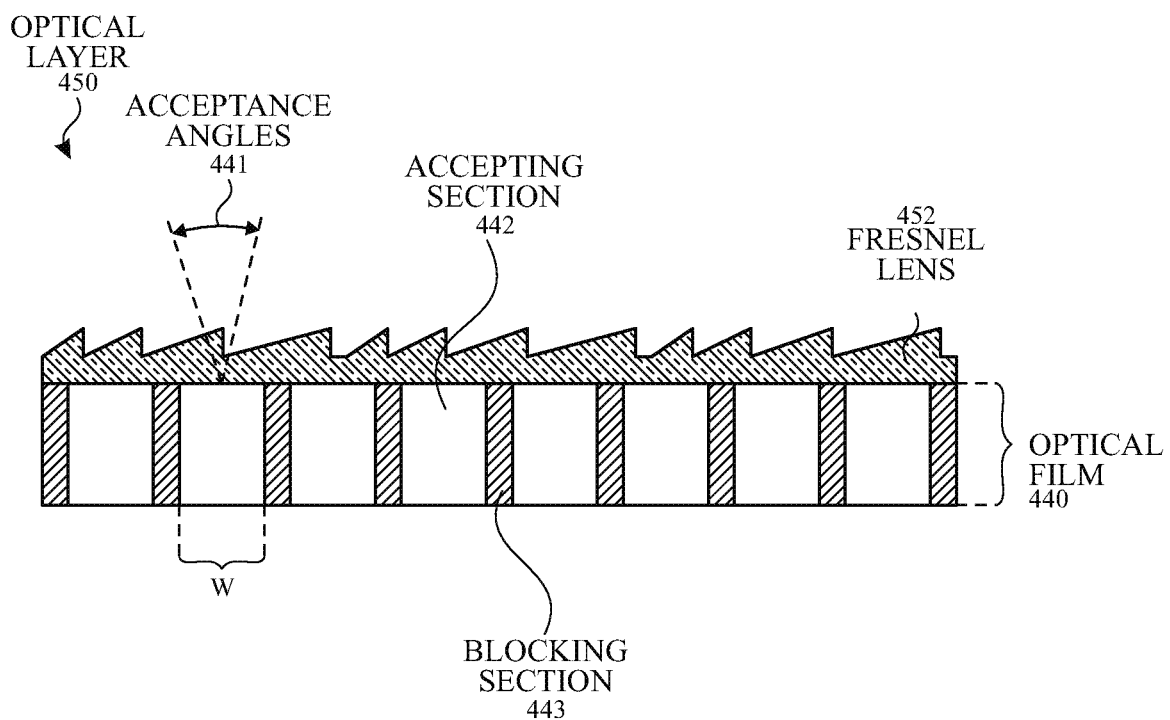
FIG. 4D illustrates a cross-sectional view of an exemplary optical layer and a Fresnel lens disposed on or located in close proximity to the optical layer according to examples of the disclosure.

In some examples, the acceptance viewing angles can be adjusted by configuring the tilt (i.e., angle formed between the blocking section and the substrate layer) of the blocking sections, as illustrated in FIG. 4C. For example, blocking section 443A can be tilted the least, while blocking section 443B can have a greater amount of tilt than blocking section 443A. In this manner, acceptance section 442A (corresponding to blocking section 443A) can be configured to accept light with narrower angles of incidence than acceptance section 442B (corresponding to blocking section 443B). In some examples, the tilt of the blocking sections can vary gradually (e.g., each blocking section 443 can have a tilt less than an adjacent blocking section 443 and a tilt greater than the other adjacent blocking section 443). In some examples, the optical film can include a plurality of blocking sections 443 with the same tilt, and each plurality can have a different tilt from other pluralities (e.g., two adjacent first blocking sections having the same first tilt, followed by two adjacent second blocking sections having the same second tilt). Examples of the disclosure can include all of the blocking sections having the same tilt.

The width(s) (e.g., width w illustrated in FIG. 4A), height (e.g., height $h_a$ illustrated in FIG. 4B), and/or tilt can be configured based on one or more properties of other components included in the device. The one or properties can include the dimensions (e.g., height and width) and material properties (e.g., refractive index) of the window, the amount of light allowed to be incident on the photodiode, the width of the opaque mask, and the separation distance(s) between light emitter(s) and light sensor(s). Examples of the disclosure can further include one or more Fresnel lenses, such as Fresnel lens 452 illustrated in FIG. 4D disposed on or in close proximity to optical film 440.

Figure 4E:
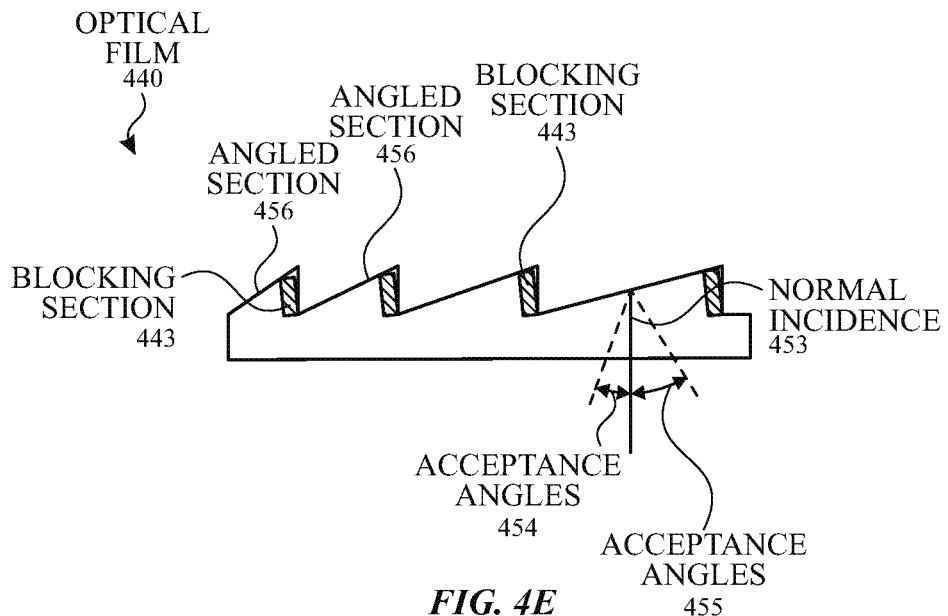
FIG. 4E illustrates an exemplary optical layer configured with direction-dependent acceptance angles according to examples of the disclosure.
Figure 4F:
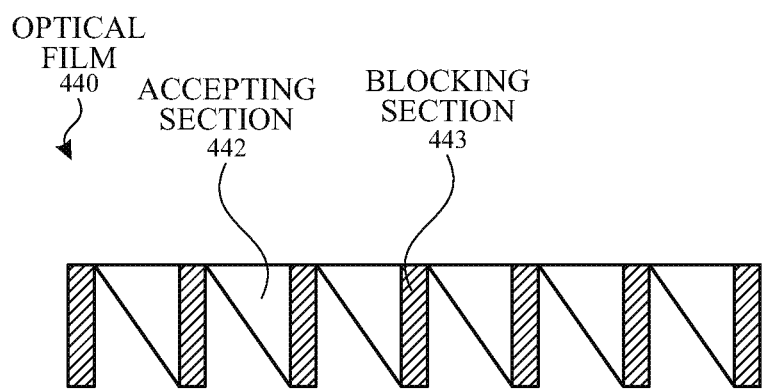
FIG. 4F illustrates an exemplary optical layer configured with triangular accepting sections according to examples of the disclosure.

In some examples, the optical film can be configured as a bi-directional optical film with direction-dependent acceptance angles. FIG. 4E illustrates an exemplary optical film configured with direction-dependent acceptance angles according to examples of the disclosure. Optical film 440 can include a plurality of blocking sections 443 configured to block light coming from a first direction (e.g., left side). The optical film 440 can include a plurality of angled sections 456 configured to allow light from the first direction having acceptance angles 454 (relative to normal incidence 453) to pass through the optical film 440. Light from the first direction having an angle of incidence outside of the acceptance angles 454 may not pass through the optical film due to total internal reflection occurring at the interface of the angled sections 456. The optical film can further be configured to allow light from a second direction (e.g., right side) having acceptance angles 455 (relative to normal incidence 453) to pass through the optical film 440. Light from the second direction having an angle of incidence outside of the acceptance angles 455 may not pass through the optical film due to total internal reflection occurring at the interface of the angled sections 456. The acceptance angles 454 and acceptance angles 455 can be varied by adjusting the angles of angled edges 456 (e.g., accepting sections), where acceptance angles 454 can be different from acceptance angles 455. For example, acceptance angles 455 can include wider viewing angles than acceptance angles 454. In this manner, the optical film 440 can be direction-dependent, and the overall range of acceptance angles of the optical film 440 can be tilted (e.g., towards the second direction). That is, the optical film 440 can accept wider viewing angles from the second direction than viewing angles accepted from the first direction. In some examples, an optical film can be configured with direction-dependent acceptance angles by including a plurality of blocking sections 443, as shown in FIG. 4F, along with accepting sections 442 having angled edges. The angled (i.e., sloped) edges can be formed by fabricating (e.g., molding, lapping, grinding, polishing, etc.) accepting sections 442 to be triangular in shape, for example.

Figure 5A:
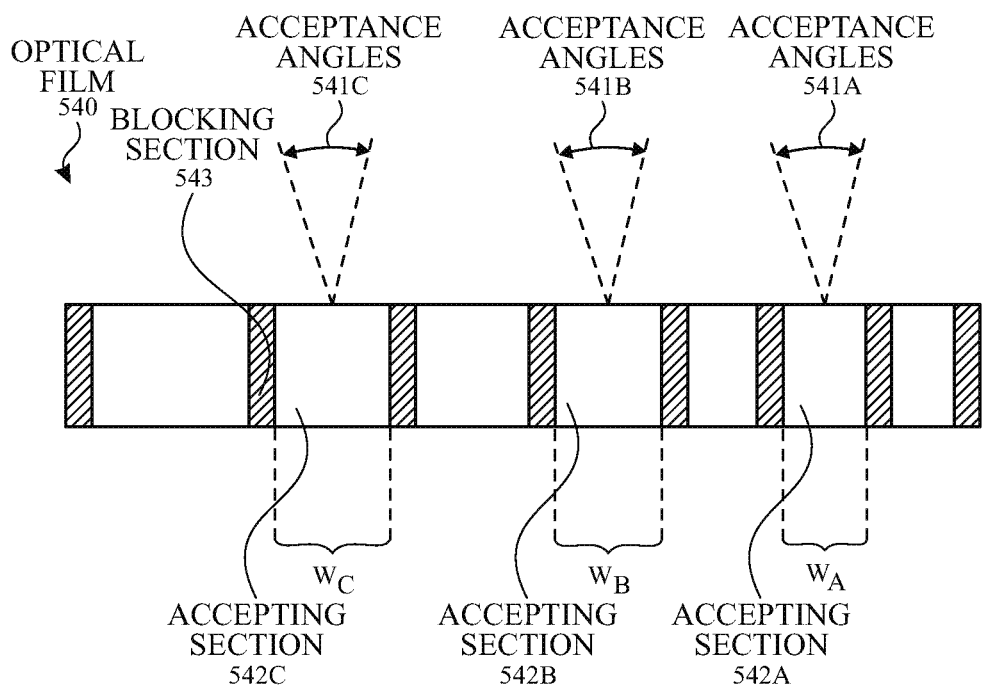
FIGS. 5A-5B illustrate cross-sectional views of an exemplary optical layer including a plurality of sets of acceptance angles and an exemplary device including the optical layer according to examples of the disclosure.
Figure 5B:
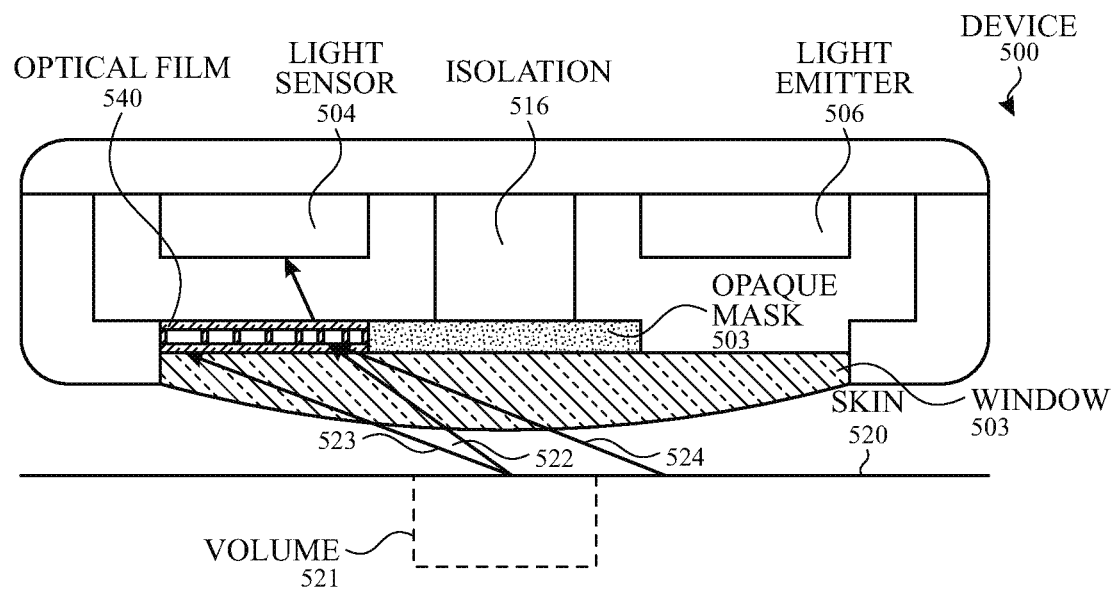

In some examples, the optical film can include a plurality of sets of accepted viewing angles. FIGS. 5A-5B illustrate cross-sectional views of an exemplary optical film including a plurality of sets of acceptance angles and an exemplary device including the optical film according to examples of the disclosure. Optical film 540 can include a plurality of accepting sections 542, each section having one or more acceptance viewing angles. The plurality of sections 542 can have different acceptance viewing angles. For example, at least one accepting section 542A can have acceptance angles 541A; at least another accepting section 542B can have acceptance angles 541B; and at least another accepting section 542C can have acceptance angles 541C. In some examples, the acceptance angles can vary depending on the location of the optical film 540 relative to the intended measurement location on skin 520 and/or other components in device 500. For example, device 500 can be configured to measure volume 521 in skin 520. To capture light from volume 521, optical film 540 can be configured to accept narrower viewing angles for sections located closer to volume 521 (e.g., closer to isolation 516 and/or light emitter 506) and wider viewing angles for sections located further away from volume 521. For example, device 500 can accept both light 522 and light 523, where the angle of incidence of light 522 is less than the angle of incidence of light 523. The same section that accepted light 522 may not accept light 524, which may have the same angle of incidence as light 523. Light 524 may have originated from an unwanted volume (e.g., a volume outside volume 521) of skin 520. In this configuration, acceptance angles 541A can be less than acceptance angles 541B, which can be less than acceptance angles 541C. In some examples, the acceptance angles can vary gradually (e.g., each accepting section 542 can have acceptance angles less than an adjacent accepting section 542 and acceptance angles greater than the other adjacent accepting section 542). In some examples, the optical film can include a plurality of accepting sections 542 with the same acceptance angles, and each plurality can different acceptance angles from other pluralities.

In some examples, the width of at least two of the plurality of sections 542 can differ. For examples, accepting section 542A corresponding to acceptance angles 541A can have a width $w_A$, which can be different from width $w_B$ corresponding to accepting section 542B having acceptance angles 541B and width $w_C$ corresponding to accepting section 542C having acceptance angles 541C. In some instances, sections (e.g., accepting section(s) 542A) of optical film 540 located closer to volume 521 (e.g., closer to isolation 516 and/or light emitter 506) can be narrower than sections (e.g., sections 542C) of optical film 540 located further away. For example, width $w_A$ can be narrower than width $w_C$. Examples of the disclosure can include variations in the widths of the accepting sections that corresponding variations in the acceptance angles (e.g., wider acceptance angles can be achieved by configuring the optical film with wider accepting sections), as discussed above.

Figure 5C:
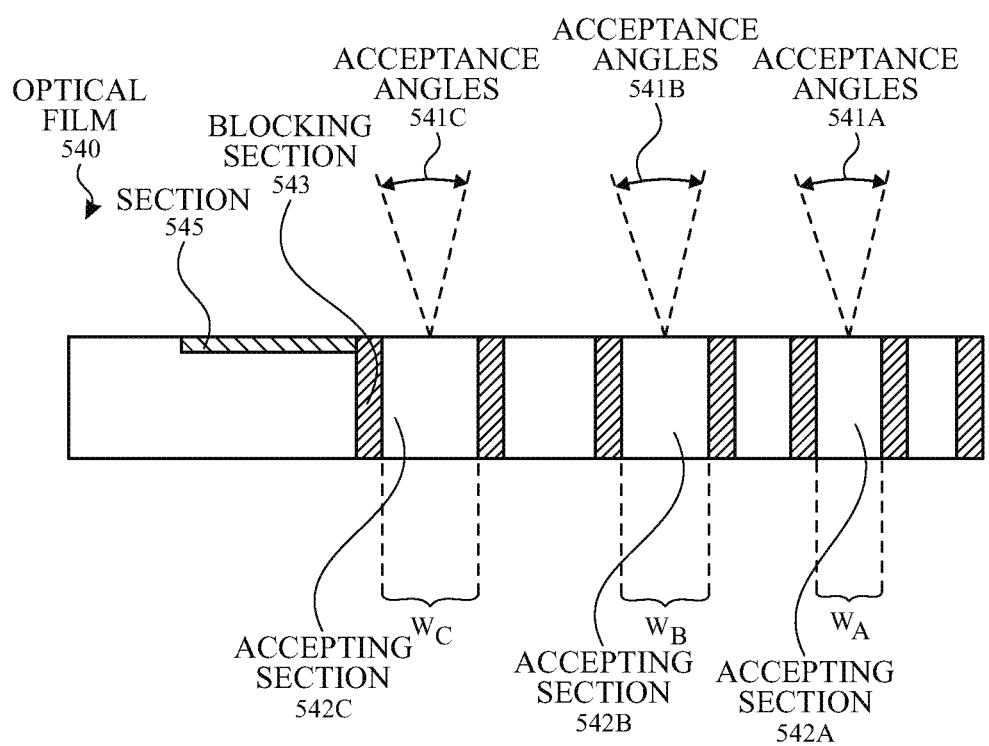
FIG. 5C illustrates a cross-sectional view of an exemplary optical layer including a section including a section having different optical properties than the accepting sections according to examples of the disclosure.

In some examples, optical film 540 can include one or more sections, such as section 545 illustrated in FIG. 5C, configured to accept light having optical properties different from the accepting sections. Section 545 can be located a pre-determined distance away from isolation 516 and/or light emitter 506. Alternatively, section 545 may be excluded from optical film 540 and may instead be an absence of material. In some examples, section 545 can include one or more materials (e.g., an infrared transparent ink) and may be separate and distinct from optical film 540. Further details with respect to section 545 are provided below.

Figure 6A:
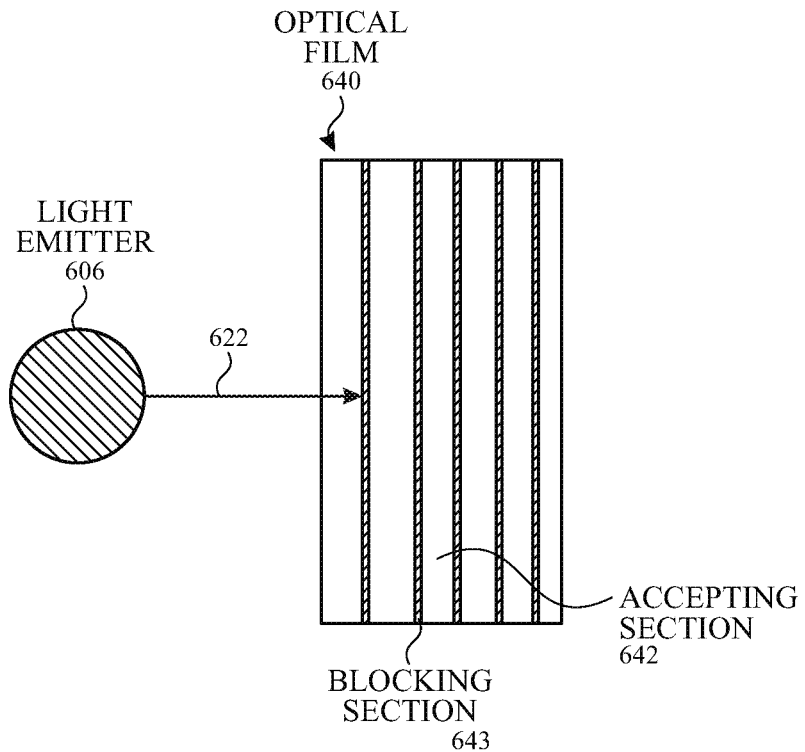
FIGS. 6A-6C illustrate top views of exemplary optical layers according to examples of the disclosure.
Figure 6B:
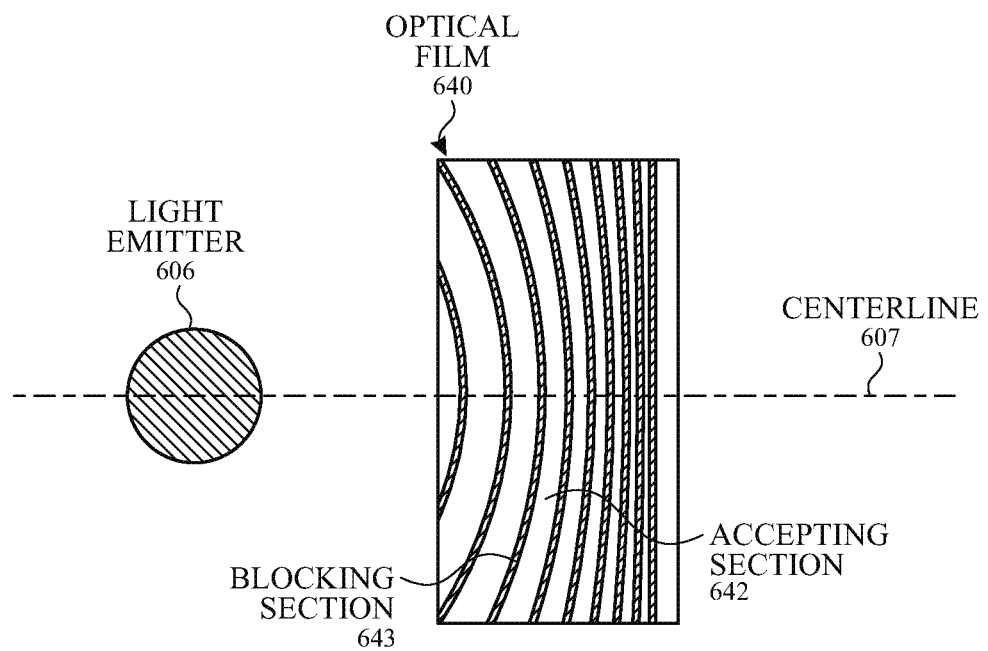

The blocking sections of the optical film can be configured based on the location of the light emitter. FIGS. 6A-6B illustrate top views of exemplary optical films according to examples of the disclosure. Optical film 640 can include a plurality of accepting sections 642 and a plurality of blocking sections 643. The block sections 643 can be straight lines or rectangles, as shown in FIG. 6A, oriented orthogonal to the direction of light 622 emitted by light emitter 606. In some examples, as illustrated in FIG. 6B, the center of the blocking sections 643 can be aligned with the center of the light emitter 606, as indicated by centerline 607. As illustrated in the figure, the curvature of the blocking sections 643 can decrease as the separation distance between a respective blocking section 643 and light emitter 606 increases.

Figure 6C:
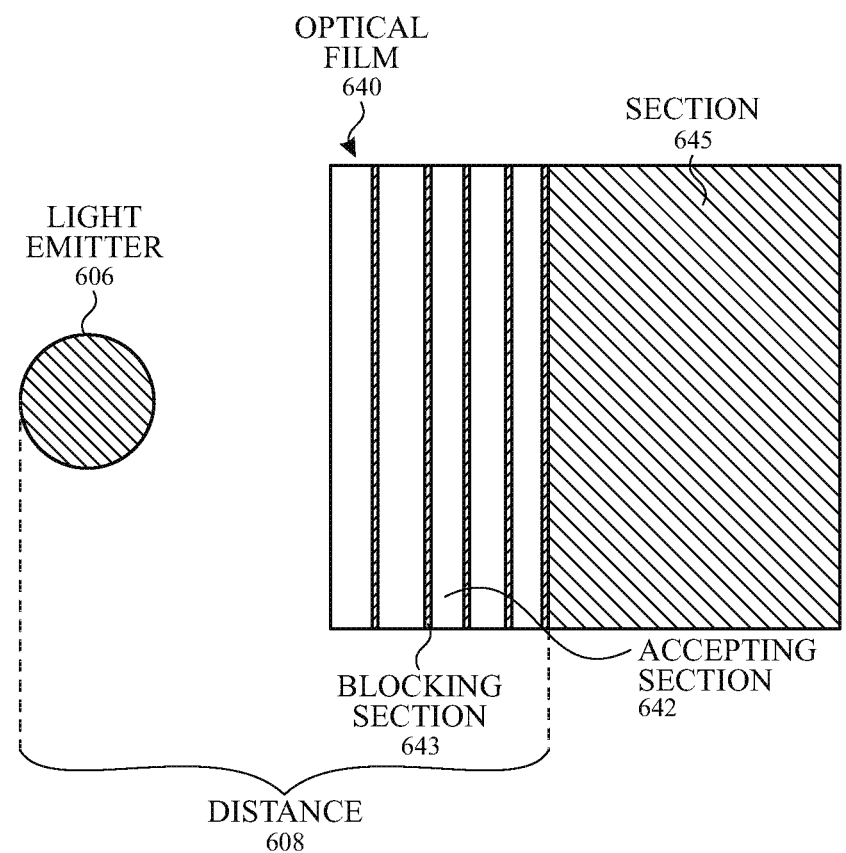

Examples of the disclosure include various configurations for the sections. For example, as illustrated in FIG. 6C, optical film 640 can include section 645. At distances shorter than a pre-determined distance 608, the optical film 640 can include a plurality of accepting sections 642 and a plurality of blocking sections 643. At distances longer than distance 608, the optical film can include section 645. Section 645 can include one or more functions and/or properties as described above with respect to section 545.

Figure 6D:
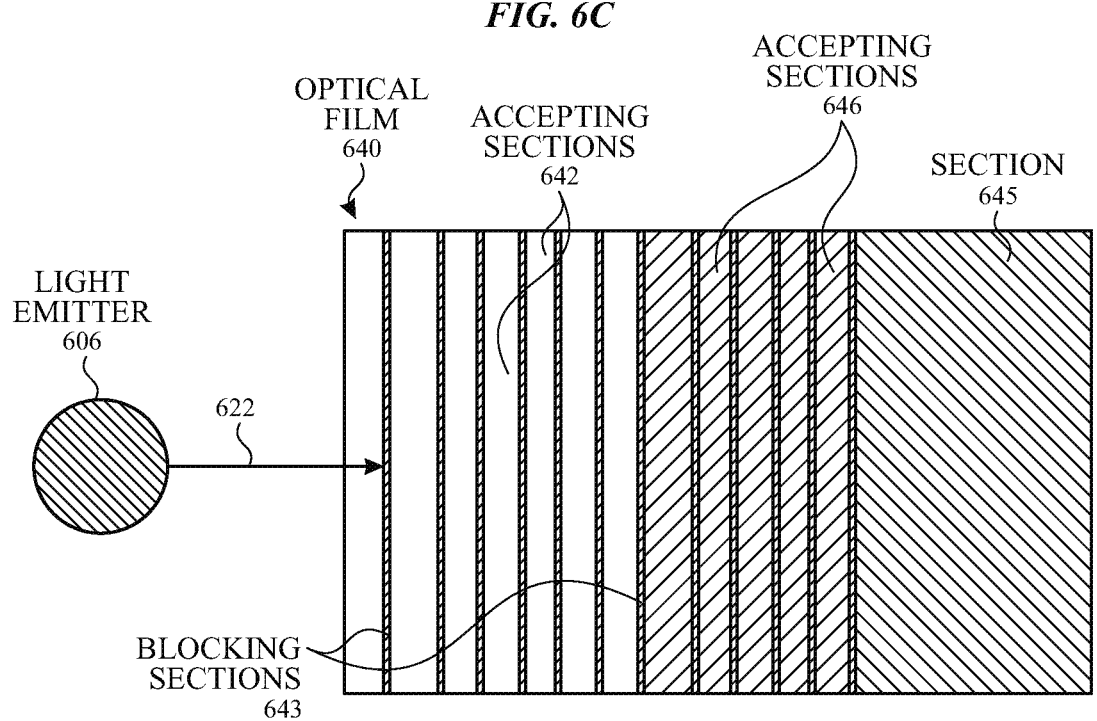
FIGS. 6D-6F illustrate top views of exemplary optical layers including two different types of accepting sections according to examples of the disclosure.
Figure 6E:
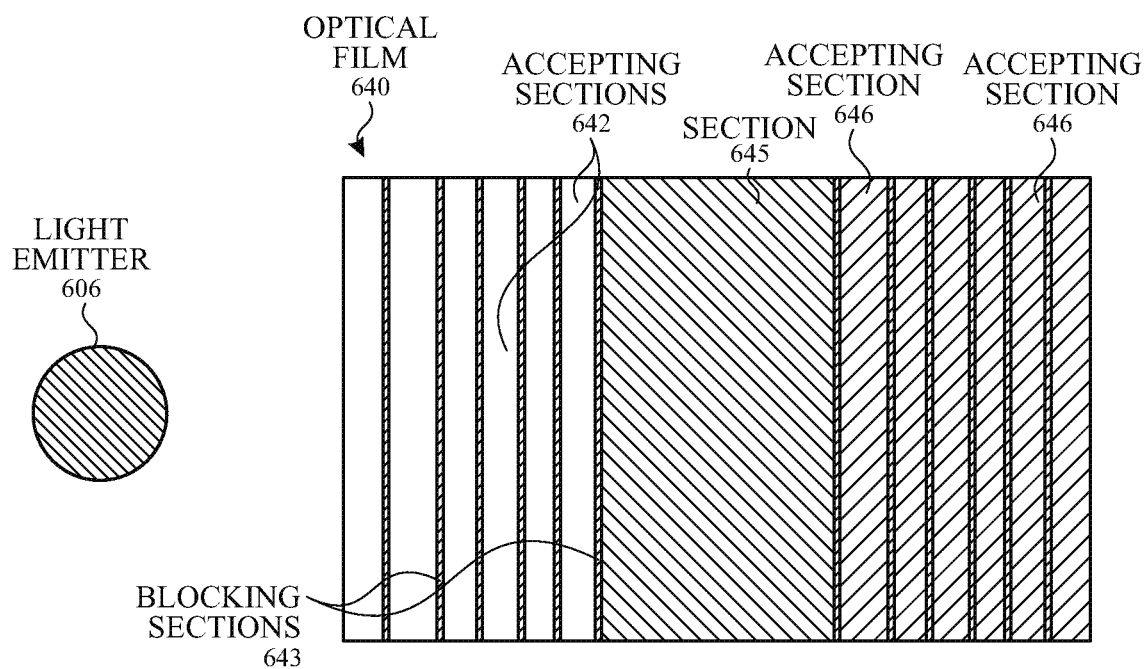
Figure 6F:
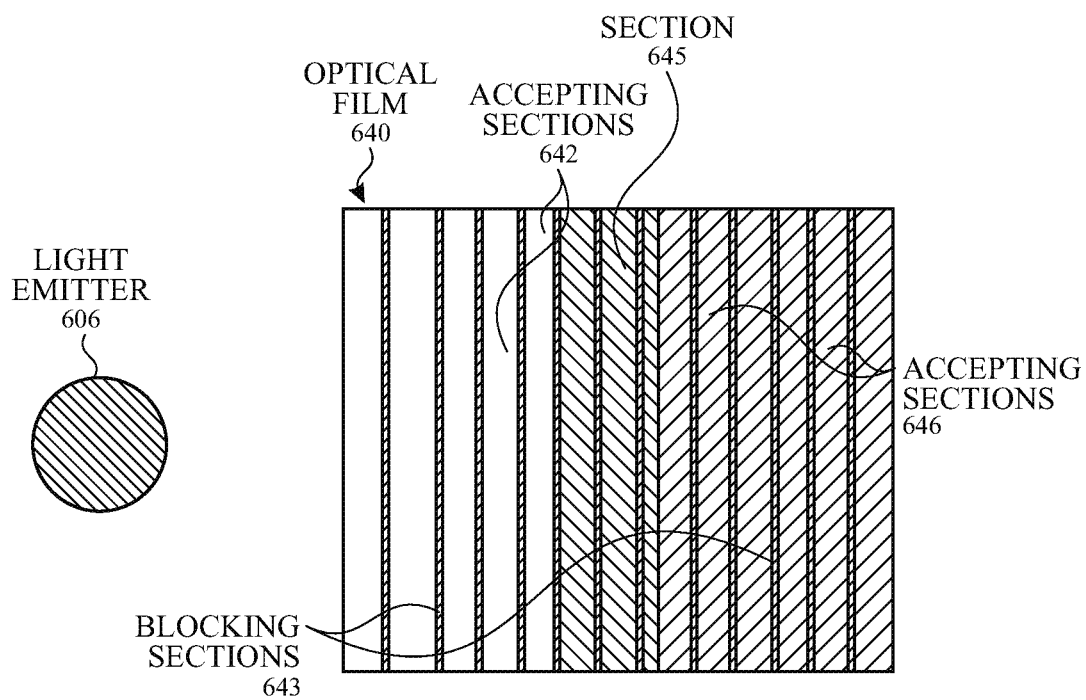

The optical film can also include multiple types of blocking sections and/or accepting sections. FIG. 6D illustrates an exemplary optical film including two different types of accepting sections: accepting sections 642 and accepting sections 646. Accepting sections 642 can have one or more properties different from accepting sections 446. For example, accepting sections 642 can include a material configured to allow one or more ranges of wavelengths (e.g., visible light) to pass through, while accepting sections 646 can include material configured to allow other ranges of wavelengths (e.g., infrared light) to pass through. In some examples, section 645 can be located on one end (e.g., the end furthest from light emitter 606), as illustrated in FIG. 6D, and in other examples, section 645 can be located between accepting sections, as illustrated in FIG. 6E. In some examples, section 645 can overlap with at least a portion of the accepting sections, as illustrated in FIG. 6F.

Figure 6G:
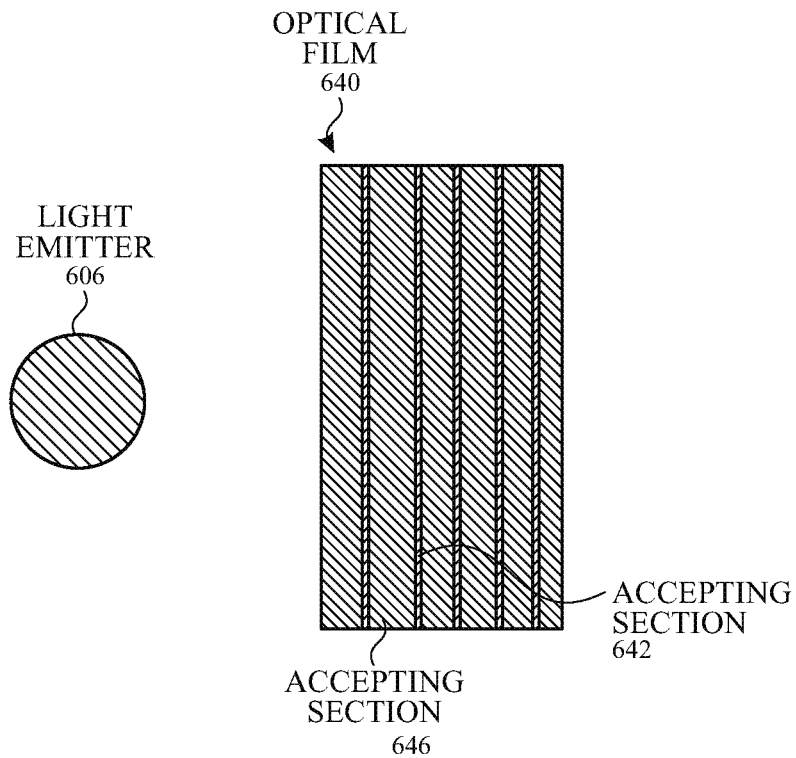
FIGS. 6G-6H illustrate top views of exemplary optical layers including accepting sections of different types having a pre-determined order according to examples of the disclosure.

In some examples, the different types of accepting sections can be interleaved (e.g., an accepting section 642, a blocking section 443, an accepting sections 646, a blocking section 443, an accepting section 642, etc.). In some examples, blocking sections can be replaced by accepting sections (e.g., an accepting section 642, an accepting section 646, an accepting section 642, an accepting section 646, etc.), as illustrated in FIG. 6G. That is, accepting sections can multi-functional configured to both accept light having one or more wavelengths and acceptance viewing angles and block light have other wavelengths and/or other viewing angles. In some examples, optical film 640 can exclude blocking sections.

Figure 6H:
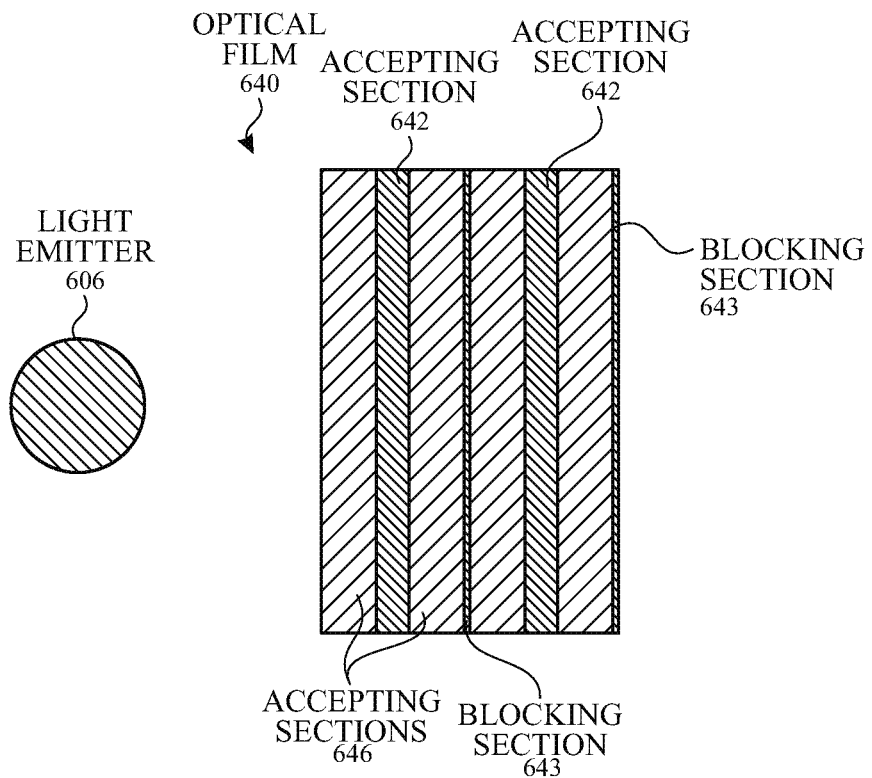

The configuration of the optical film can include any ordering of the accepting section(s) and blocking section(s). The order can depend on several factors, such as the desired amount of light to pass through to the light sensor, the amount of noise and/or crosstalk, the placement of the light emitters, etc. As a non-limiting example, FIG. 6H illustrates optical film 640 with the sections ordered as two adjacent accepting sections of differing type next to a block section (e.g., accepting section 646, accepting section 642, accepting section 646, blocking section 643, accepting section 646, accepting section 642, accepting section 646, blocking section 643, etc.) Examples of the disclosure including any order and configurations of the sections such that the total area of accepting sections configured for visible transparency is greater than the total area of accepting sections configured for infrared transparency.

Figure 7A:
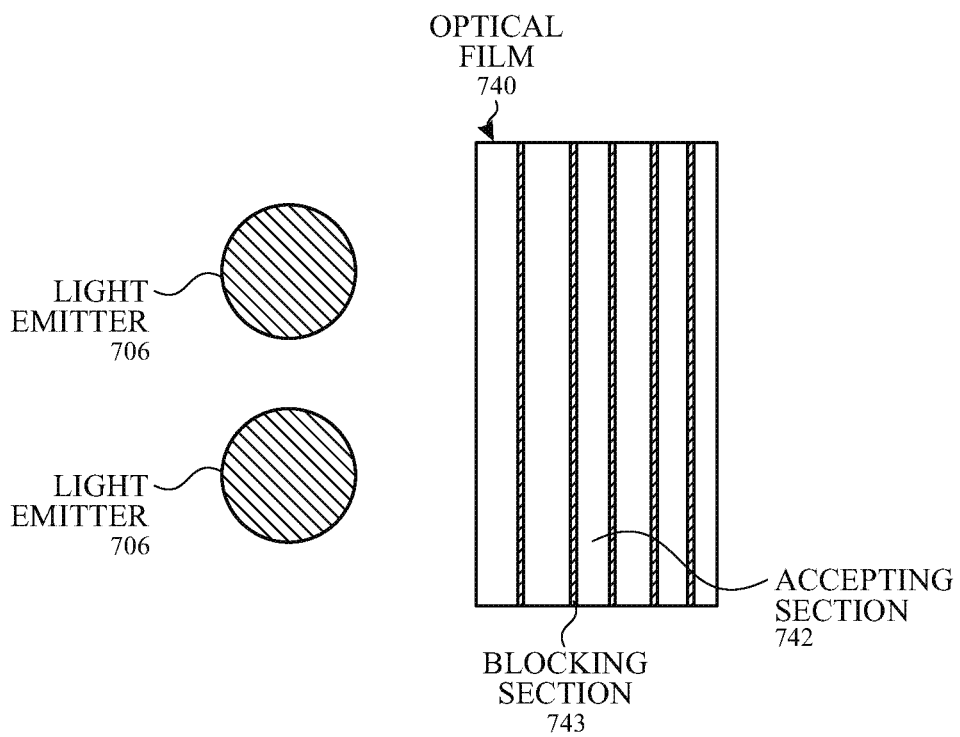
FIGS. 7A-7B illustrate top views of exemplary optical layers configured for multiple light emitters according to examples of the disclosure.
Figure 7B:
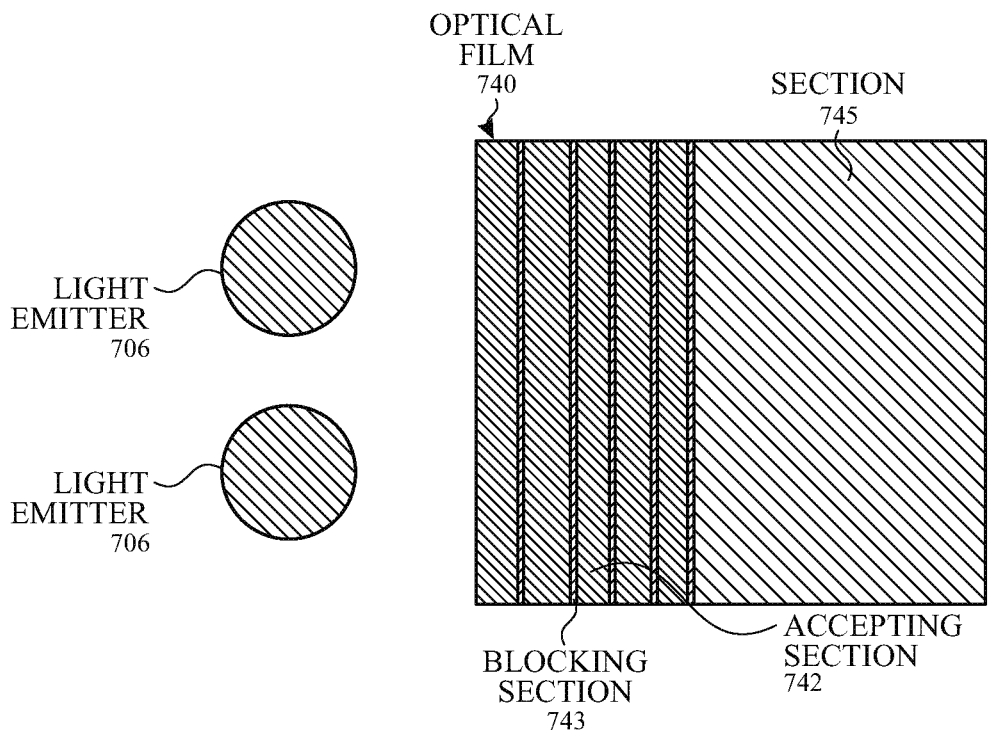

In some examples, the same optical film can be optically coupled to multiple light emitters. FIGS. 7A-7B illustrate top views of exemplary optical films configured for multiple light emitters according to examples of the disclosure. Optical film 740 can restrict acceptance viewing angles for both light emitters 706. In some examples, as illustrated in FIG. 7B, optical film 740 can include another section 745, which can include a material different from accepting sections 742, can exclude a material, and/or can be separate and distinct from optical film 740. For example, section 745 can include one or more properties and/or functions as section 545 (illustrated in FIG. 5D). For example, section 745 can include an infrared transparent material configured to allow infrared light to pass through to the light sensor for proximity sensing (e.g., off-wrist detection). The infrared transparent ink can be configured to allow infrared light to pass through to the light sensor, while also configured to at least partially block the user's view (e.g., a material that absorbs or blocks visible light).

Figure 7C:
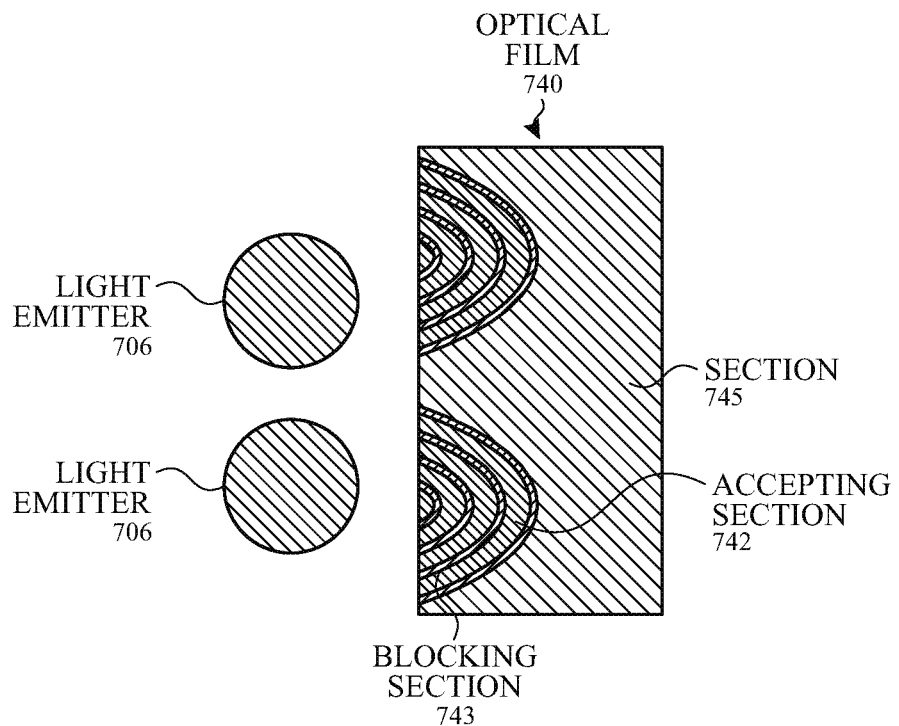
FIGS. 7C-7D illustrate top views of exemplary optical layers including curved blocking sections according to examples of the disclosure.
Figure 7D:
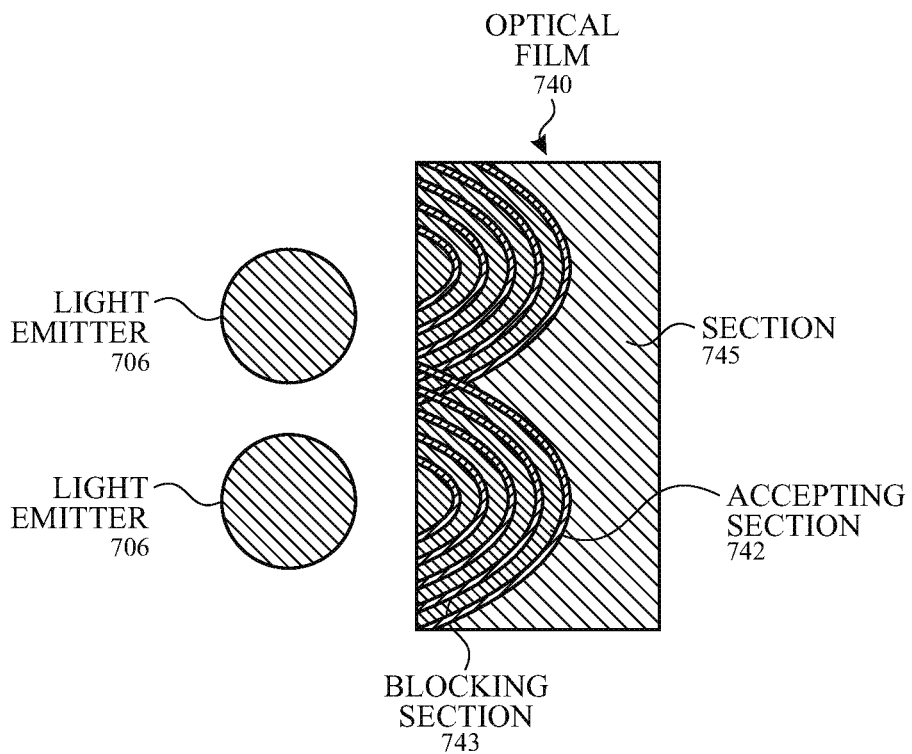

Although the figure illustrates blocking sections oriented along one direction as straight lines, examples of the disclosure can include any configuration, shape, and/or size of blocking sections and accepting sections as discussed throughout the disclosure. FIG. 7C illustrates a top view of an exemplary optical film including curved blocking sections with the center of the blocking sections 743 aligned with the center of its respective light emitter 706. In some examples, optical film 740 can include section 745. In some examples, the accepting sections of the different light emitters can overlap, at least partially, as shown in FIG. 7D. Overlapping the accepting sections may include forming one section on top of another in the stackup, thereby creating multiple layers disposed on the window (not shown).

Figure 7E:
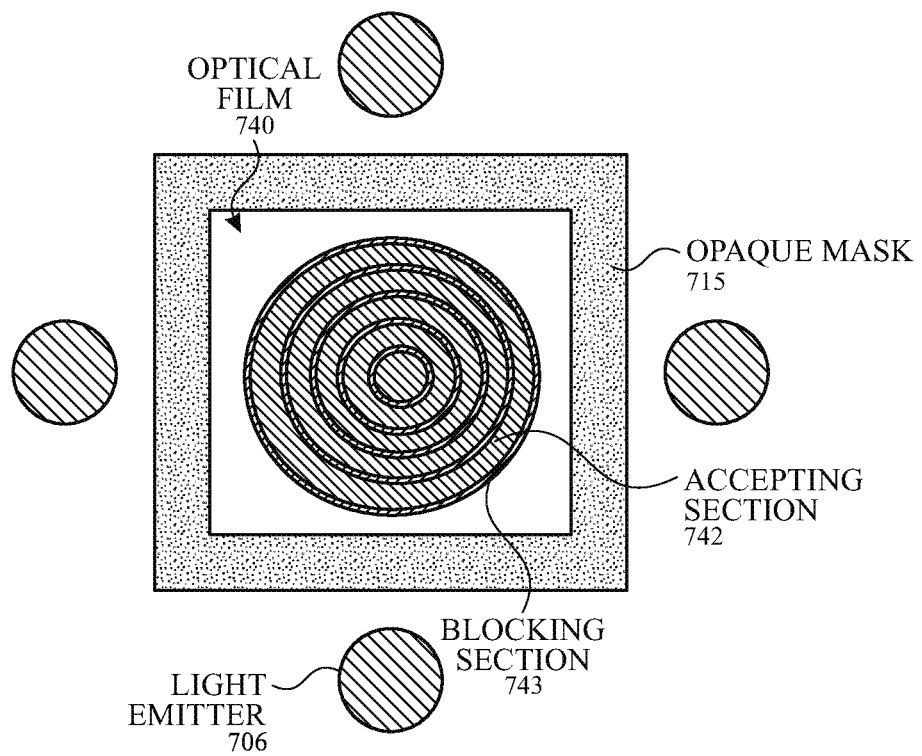
FIGS. 7E-7L illustrate top views of exemplary optical layers with various configurations for a device including multiple light emitters according to examples of the disclosure.
Figure 7F:
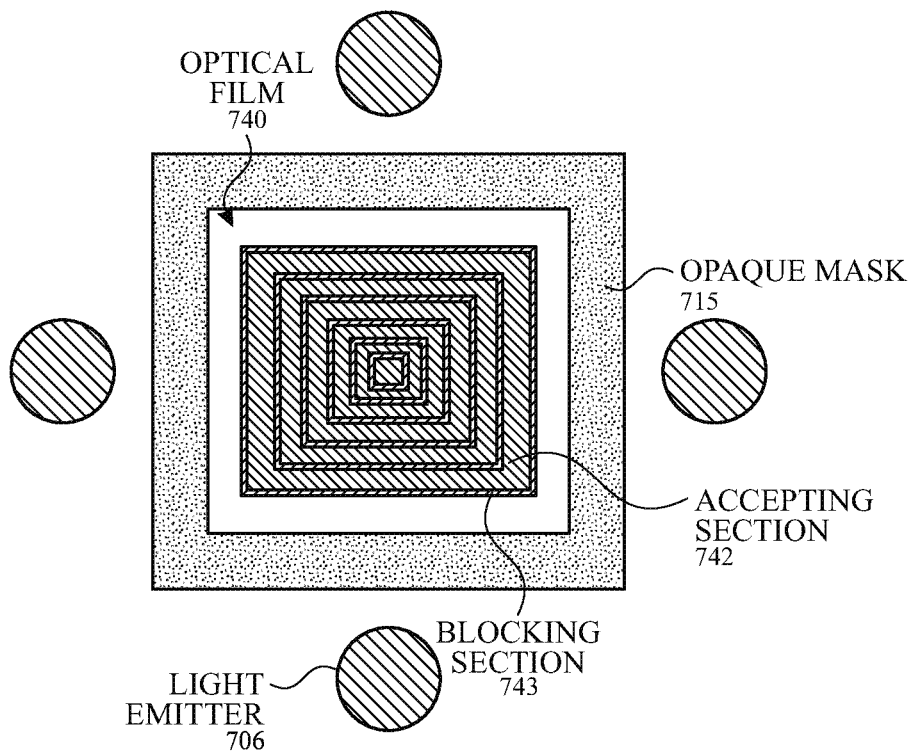
Figure 7G:
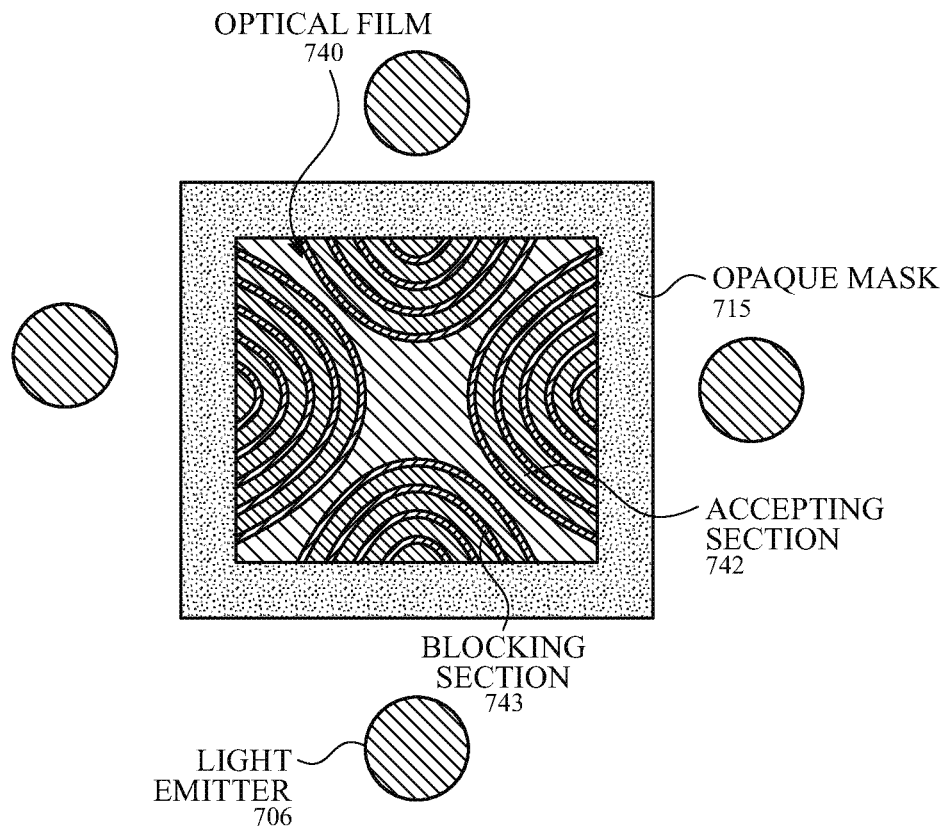
Figure 7H:
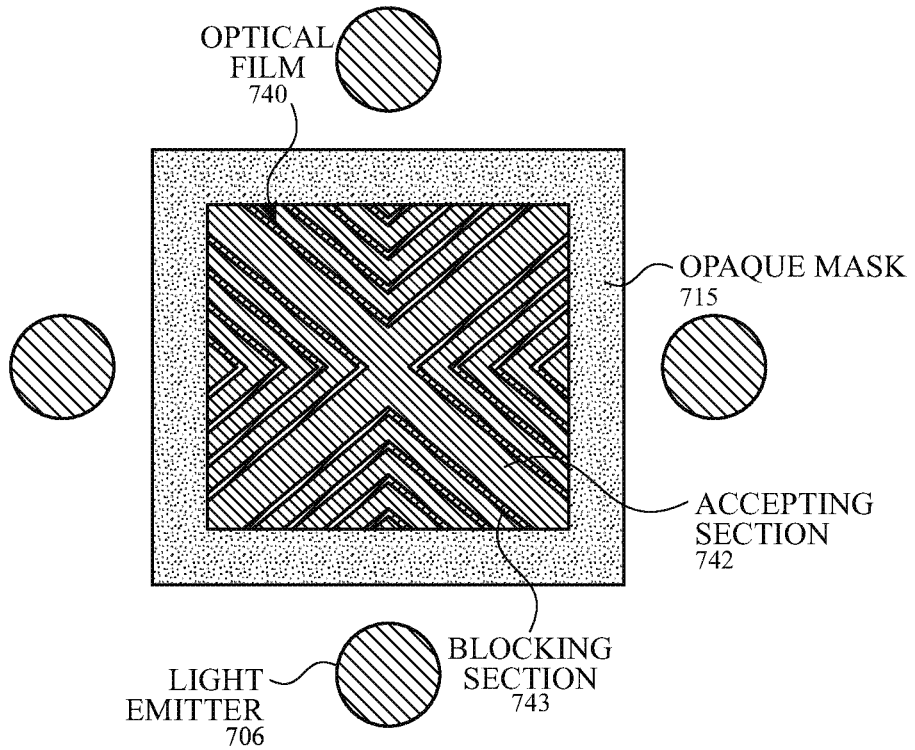
Figure 7I:
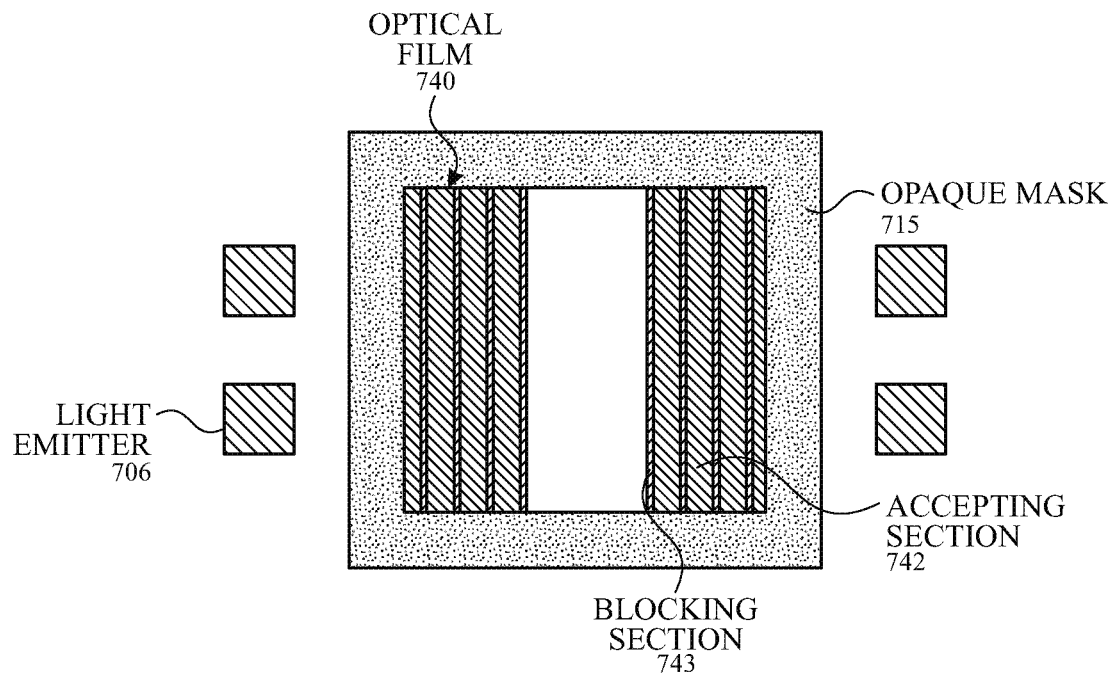
Figure 7J:
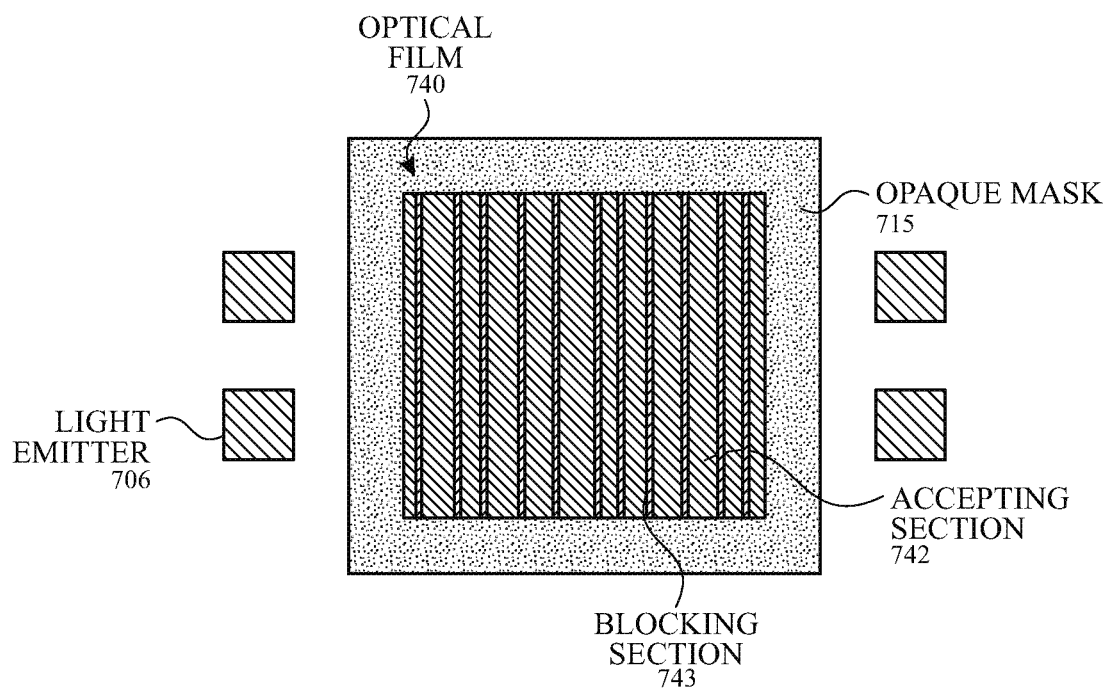
Figure 7K:
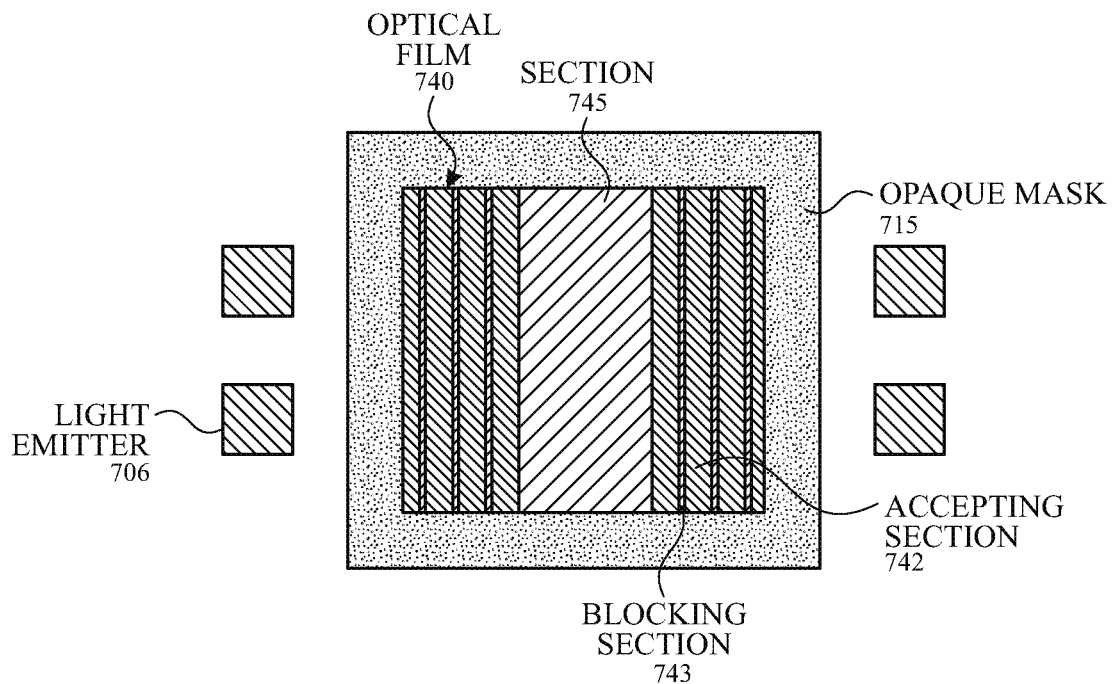
Figure 7L:
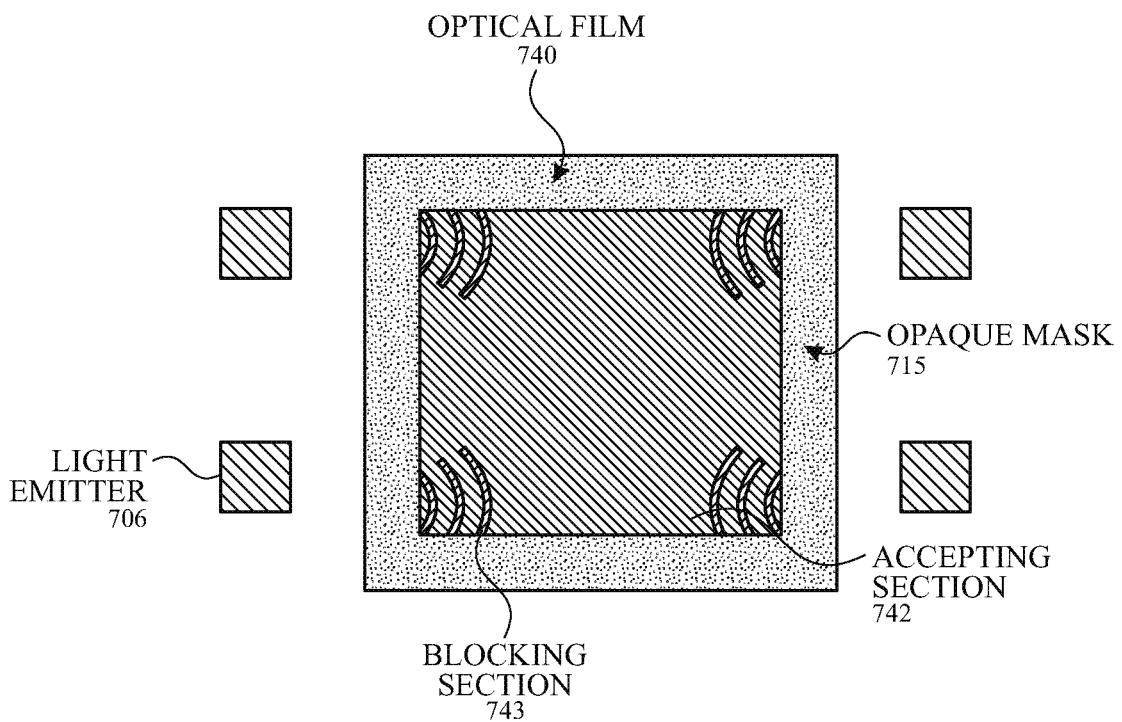

The optical film can be optically coupled to light emitters located on different sizes of the optical film. FIGS. 7E-7H illustrate top views of exemplary optical films with various configurations for a device including multiple light emitters according to examples of the disclosure. The blocking sections of the optical film can be configured to be anisotropic to prevent blocking of light from the user's skin that can include useful physiological information. For example, the accepting sections 742 and blocking sections 743 can be configured as any shape including, but not limited to, circles (as illustrated in FIG. 7E), squares/rectangles (as illustrated in FIG. 7F), arcs (as illustrated in FIG. 7G), or triangles (as illustrated in FIG. 7H). The center the blocking sections 743 can be located in the center of the optical film 740 (as illustrated in FIGS. 7E-7H) or can be aligned with the center of the optical components (as illustrated in FIGS. 7I-7K). Furthermore, optical film 740 can include multiple different types of shapes. Additionally or alternatively, optical film 740 can exclude section 745 (as illustrated in FIGS. 7I-7J) or can include section 745 between sections (as illustrated in FIG. 7K). In some examples, multiple areas of the optical film can be spatially separated by an absence of material (as illustrated in FIG. 7I). In some examples, blocking sections may not form closed shapes and/or may not extend from one side of the optical film to the other, as illustrated in FIG. 7L.

As illustrated in the figures and discussed above and below, the optical film and/or optical layer can have spatially varying asymmetry in its structural and/or optical properties. Additionally, including light emitters configured to emit various wavelengths (e.g., visible and infrared) of light, the device can be a multi-functional device with minimal or reduced crosstalk between the light emitters and light sensors, thereby enhancing the measurement accuracy. The multiple functions can include, but are not limited to, physiological information determination (e.g., heart rate, background heart rate, etc.) and off-wrist detection. Further, although the figures illustrate a single-pixel light sensor, examples of the disclosure can include light sensors having multiple pixels.

Although process steps or method steps can be described in a sequential order, such processes and methods can be configured to work in any suitable order. In other words, any sequence or order of steps that can be described in the disclosure does not, in and of itself, indicate a requirement that the steps be performed in that order. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modification thereto, does not imply that the illustrated process or any of its steps are necessary to one or more of the examples, and does not imply that the illustrated process is preferred.

Figure 8A:
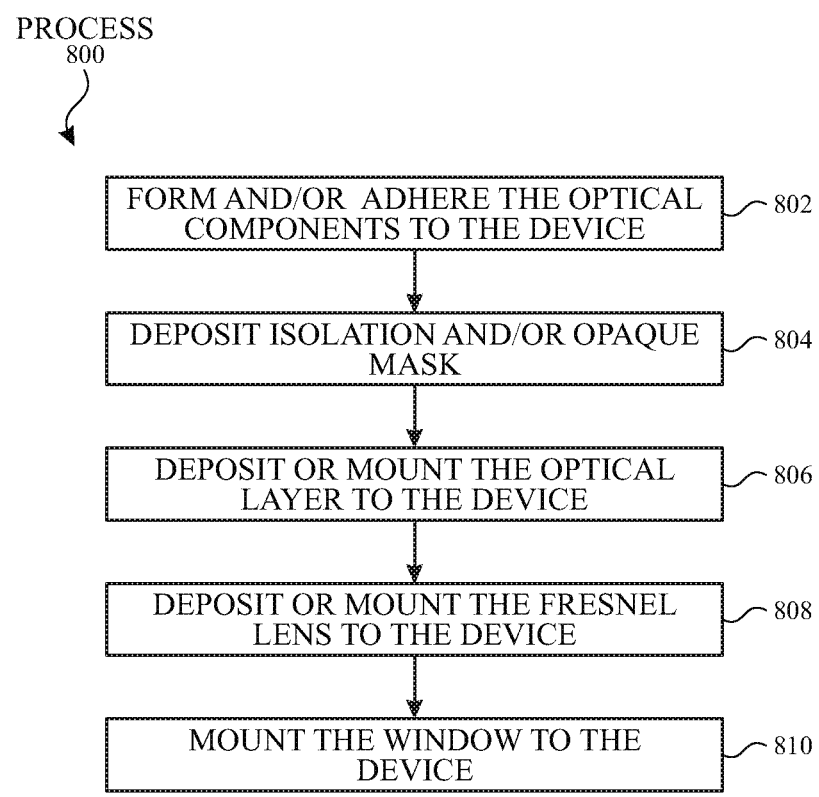
FIG. 8A illustrates an exemplary process for manufacturing a device including the optical layers described in this disclosure.

The optical layers, optical films, lens, window systems described above can be manufactured using various different fabrication techniques. FIG. 8A illustrates an exemplary process for manufacturing a device including the optical layers described in this disclosure. Process 800 can include forming and/or adhering the light emitter(s) (e.g., light emitter 306 illustrated in FIG. 3A) and light sensor(s) (e.g., light sensor 304 illustrated in FIG. 3A) in one or more cavities included in the device (step 802). The isolation (e.g., isolation 316 illustrated in FIG. 3A) and/or opaque mask 315 (e.g., isolation 315 illustrated in FIG. 3A) can be deposited (step 804). Optical layer (e.g., optical layer 350 illustrated in FIGS. 3A-3B) can be deposited or mounted to the device (step 806). In some examples, the optical layer can be formed on the light sensor. In some examples, the optical layer can be formed on the window. In some examples, forming the optical layer can include forming the accepting sections and blocking sections between substrate layers (not shown). A Fresnel lens (e.g., Fresnel lens 352 illustrated in FIG. 3D) can be deposited or mounted to one or more components (e.g., light emitter 306 illustrated in FIG. 3D), optical film 440 illustrated in FIG. 4D, etc.) of the device (step 808). In some examples, optical layer can be a single layer including multiple components (e.g., optical film, opaque mask, Fresnel lens, etc.) formed in a single processing step. The window can be adhered/mounted to the device (step 810) either before or after the optical layer is deposited.

Figure 8B:
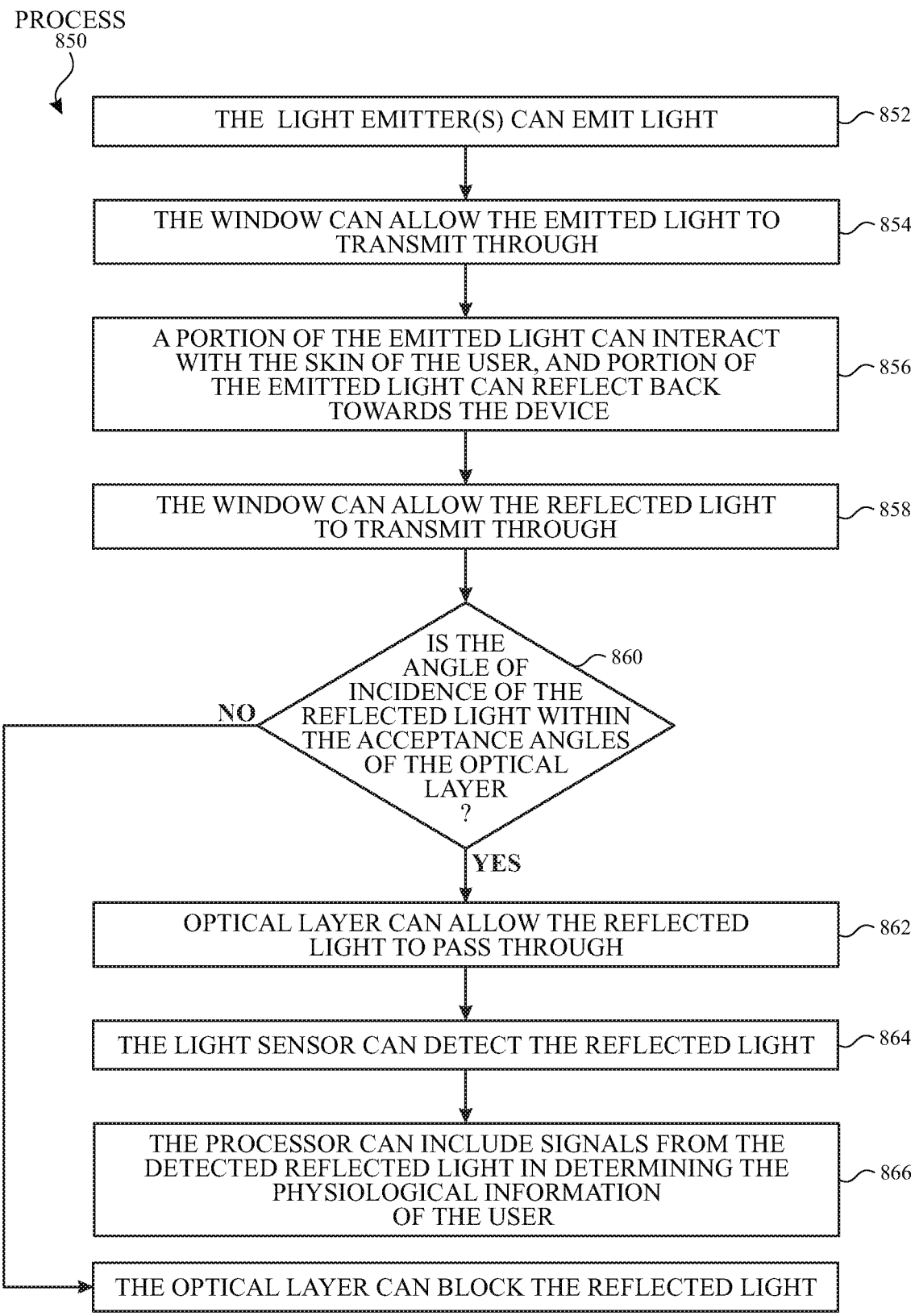
FIG. 8B illustrates an exemplary operation of the device including the optical layer according to examples of the disclosure.

FIG. 8B illustrates an exemplary operation of the device including the optical layer according to examples of the disclosure. Process 850 includes emitting light from the light emitter (step 852). The window can allow the emitted light to transmit through the window (step 854). Optionally, the emitted light further transmits through a Fresnel lens. A portion of the emitted light can interact with the skin of the user, and a portion can reflect back towards the device (step 856). The window can allow the reflected light to transmit through the window (step 858). The optical layer can accept the reflected light if the angle of incidence is within the acceptance angles (step 860). Otherwise, the optical layer can prevent (e.g., absorb or reflect back) the reflected light from transmitting through the optical layer (step 862). The accepted reflected light can be detected by the light sensor (step 864), and the processor can include signals from the detected reflected light in determining the physiological information of the user (step 866). Examples of the disclosure can further include the optical layer allowing infrared light to transmit through to the light sensor, the light sensor detecting the infrared light and generating a signal indicative of the infrared light, and the processor executing one or more instructions related to off-wrist detection.

Figure 9:
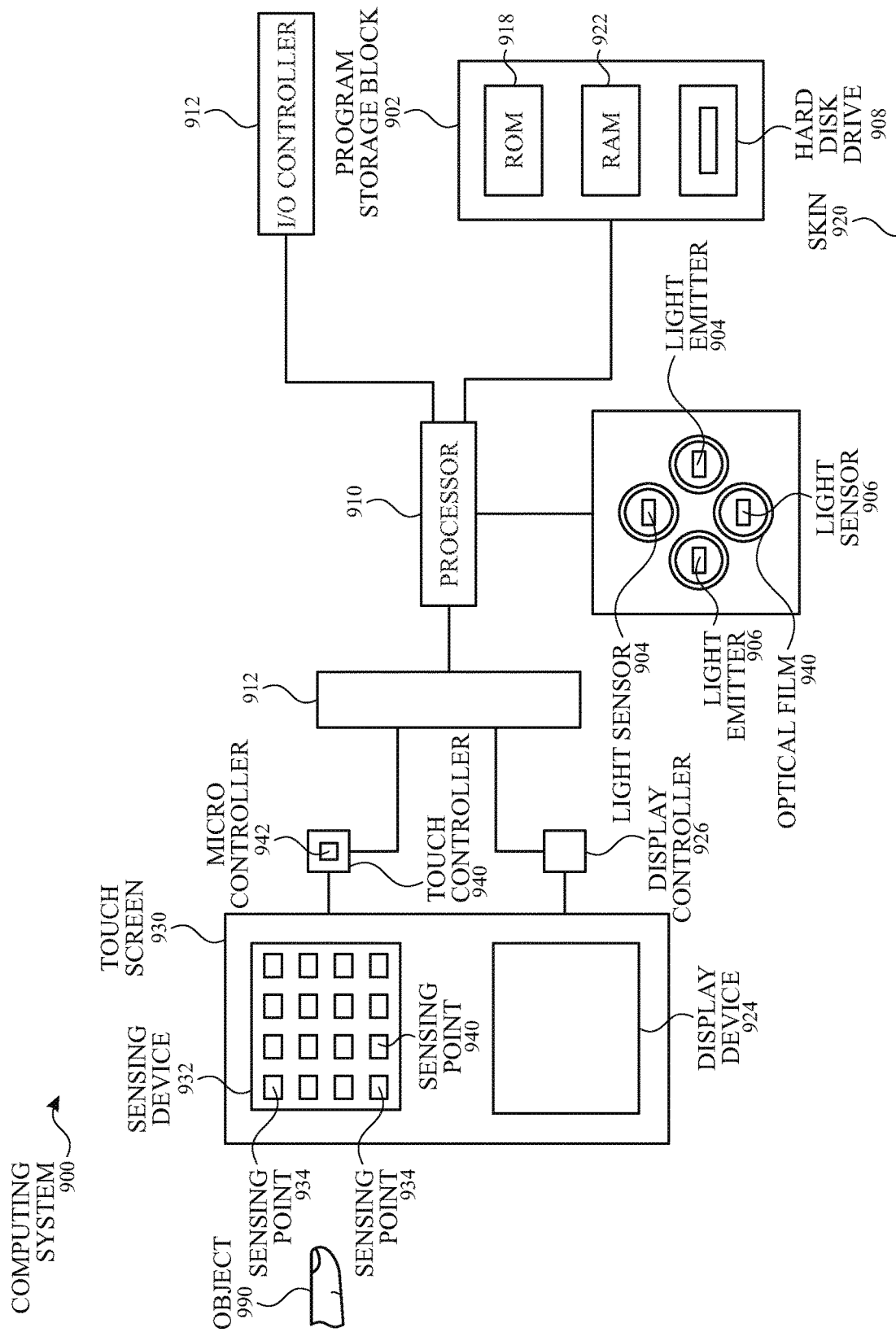
FIG. 9 illustrates an exemplary block diagram of a computing system comprising light emitters and light sensors for measuring a signal associated with a user's physiological state according to examples of the disclosure.

FIG. 9 illustrates an exemplary block diagram of a computing system comprising light emitters and light sensors for measuring a signal associated with a user's physiological state according to examples of the disclosure. Computing system 900 can correspond to any of the computing devices illustrated in FIGS. 1A-1C. Computing system 900 can include a processor 910 configured to execute instructions and to carry out operations associated with computing system 900. For example, using instructions retrieved from memory, processor 910 can control the reception and manipulation of input and output data between components of computing system 900. Processor 910 can be a single-chip processor or can be implemented with multiple components.

In some examples, processor 910 together with an operating system can operate to execute computer code and produce and use data. The computer code and data can reside within a program storage block 902 that can be operatively coupled to processor 910. Program storage block 902 can generally provide a place to hold data that is being used by computing system 900. Program storage block 902 can be any non-transitory computer-readable storage medium, and can store, for example, history and/or pattern data relating to physiological information measured by one or more light sensors such as light sensors 904. By way of example, program storage block 902 can include Read-Only Memory (ROM) 918, Random-Access Memory (RAM) 922, hard disk drive 908 and/or the like. The computer code and data could also reside on a removable storage medium and loaded or installed onto the computing system 900 when needed. Removable storage mediums include, for example, CD-ROM, DVD-ROM, Universal Serial Bus (USB), Secure Digital (SD), Compact Flash (CF), Memory Stick, Multi-Media Card (MMC) and a network component.

Computing system 900 can also include an input/output (I/O) controller 912 that can be operatively coupled to processor 910, or it can be a separate component as shown. I/O controller 912 can be configured to control interactions with one or more I/O devices. I/O controller 912 can operate by exchanging data between processor 910 and the I/O devices that desire to communicate with processor 910. The I/O devices and I/O controller 912 can communicate through a data link. The data link can be a one-way link or a two-way link. In some cases, I/O devices can be connected to I/O controller 912 through wireless connections. By way of example, a data link can correspond to PS/2, USB, Firewire, IR, RF, Bluetooth or the like.

Computing system 900 can include a display device 924 that can be operatively coupled to processor 910. Display device 924 can be a separate component (peripheral device) or can be integrated with processor 910 and program storage block 902 to form a desktop computer (e.g., all-in-one machine), a laptop, handheld or tablet computing device of the like. Display device 924 can be configured to display a graphical user interface (GUI) including perhaps a pointer or cursor as well as other information to the user. By way of example, display device 924 can be any type of display including a liquid crystal display (LCD), an electroluminescent display (ELD), a field emission display (FED), a light emitting diode display (LED), an organic light emitting diode display (OLED) or the like.

Display device 924 can be coupled to display controller 926 that can be coupled to processor 910. Processor 910 can send raw data to display controller 926, and display controller 926 can send signals to display device 924. Data can include voltage levels for a plurality of pixels in display device 924 to project an image. In some examples, processor 910 can be configured to process the raw data.

Computing system 900 can also include a touch screen 930 that can be operatively coupled to processor 910. Touch screen 930 can be a combination of sensing device 932 and display device 924, where the sensing device 932 can be a transparent panel that is positioned in front of display device 924 or integrated with display device 924. In some cases, touch screen 930 can recognize touches and the position and magnitude of touches on its surface. Touch screen 930 can report the touches to processor 910, and processor 910 can interpret the touches in accordance with its programming. For example, processor 910 can perform tap and event gesture parsing and can initiate a wake of the device or powering on one or more components in accordance with a particular touch.

Touch screen 930 can be coupled to a touch controller 940 that can acquire data from touch screen 930 and can supply the acquired data to processor 910. In some cases, touch controller 940 can be configured to send raw data to processor 910, and processor 910 can process the raw data. For example, processor 910 can receive data from touch controller 940 and can determine how to interpret the data. The data can include the coordinates of a touch as well as pressure exerted. In some examples, touch controller 940 can be configured to process raw data itself. That is, touch controller 940 can read signals from sensing points 934 located on sensing device 932 and can turn the signals into data that the processor 910 can understand.

Touch controller 940 can include one or more microcontrollers such as microcontroller 942, each of which can monitor one or more sensing points 934. Microcontroller 942 can, for example, correspond to an application specific integrated circuit (ASIC), which works with firmware to monitor the signals from sensing device 932, process the monitored signals, and report this information to processor 910.

One or both display controller 926 and touch controller 940 can perform filtering and/or conversion processes. Filtering processes can be implemented to reduce a busy data stream to prevent processor 910 from being overloaded with redundant or non-essential data. The conversion processes can be implemented to adjust the raw data before sending or reporting them to processor 910.

In some examples, sensing device 932 can be based on capacitance. When two electrically conductive members come close to one another without actually touching, their electric fields can interact to form a capacitance. The first electrically conductive member can be one or more of the sensing points 934, and the second electrically conductive member can be an object 990 such as a finger. As object 990 approaches the surface of touch screen 930, a capacitance can form between object 990 and one or more sensing points 934 in close proximity to object 990. By detecting changes in capacitance at each of the sensing points 934 and noting the position of sensing points 934, touch controller 940 can recognize multiple objects, and determine the location, pressure, direction, speed, and acceleration of object 990 as it moves across the touch screen 930. For example, touch controller 990 can determine whether the sensed touch is a finger, tap, or an object covering the surface.

Sensing device 932 can be based on self-capacitance or mutual capacitance. In self-capacitance, each of the sensing points 934 can be provided by an individually charged electrode. As object 990 approaches the surface of the touch screen 930, the object can capacitively couple to those electrodes in close proximity to object 990, thereby stealing charge away from the electrodes. The amount of charge in each of the electrodes can be measured by the touch controller 940 to determine the position of one or more objects when they touch or hover over the touch screen 930. In mutual capacitance, sensing device 932 can include a two layer grid of spatially separated lines or wires (not shown), although other configurations are possible. The upper layer can include lines in rows, while the lower layer can include lines in columns (e.g., orthogonal). Sensing points 934 can be provided at the intersections of the rows and columns. During operation, the rows can be charged, and the charge can capacitively couple from the rows to the columns. As object 990 approaches the surface of the touch screen 930, object 990 can capacitively couple to the rows in close proximity to object 990, thereby reducing the charge coupling between the rows and columns. The amount of charge in each of the columns can be measured by touch controller 940 to determine the position of multiple objects when they touch the touch screen 930.

Computing system 900 can also include one or more light emitters such as light emitters 906 and one or more light sensors such as light sensors 904 proximate to skin 920 of a user. Light emitters 906 can be configured to generate light, and light sensors 904 can be configured to measure a light reflected or absorbed by skin 920, vasculature, and/or blood of the user. Device 900 can include optical film 940 coupled to light emitters 906. Light sensor 904 can send measured raw data to processor 910, and processor 910 can perform noise and/or artifact cancelation to determine the signals. Processor 910 can dynamically activate light emitters and/or light sensors based on an application, user skin type, and usage conditions. In some examples, some light emitters and/or light sensors can be activated, while other light emitters and/or light sensors can be deactivated to conserve power, for example. In some examples, processor 910 can store the raw data and/or processed information in a ROM 918 or RAM 922 for historical tracking or for future diagnostic purposes.

Figure 10:
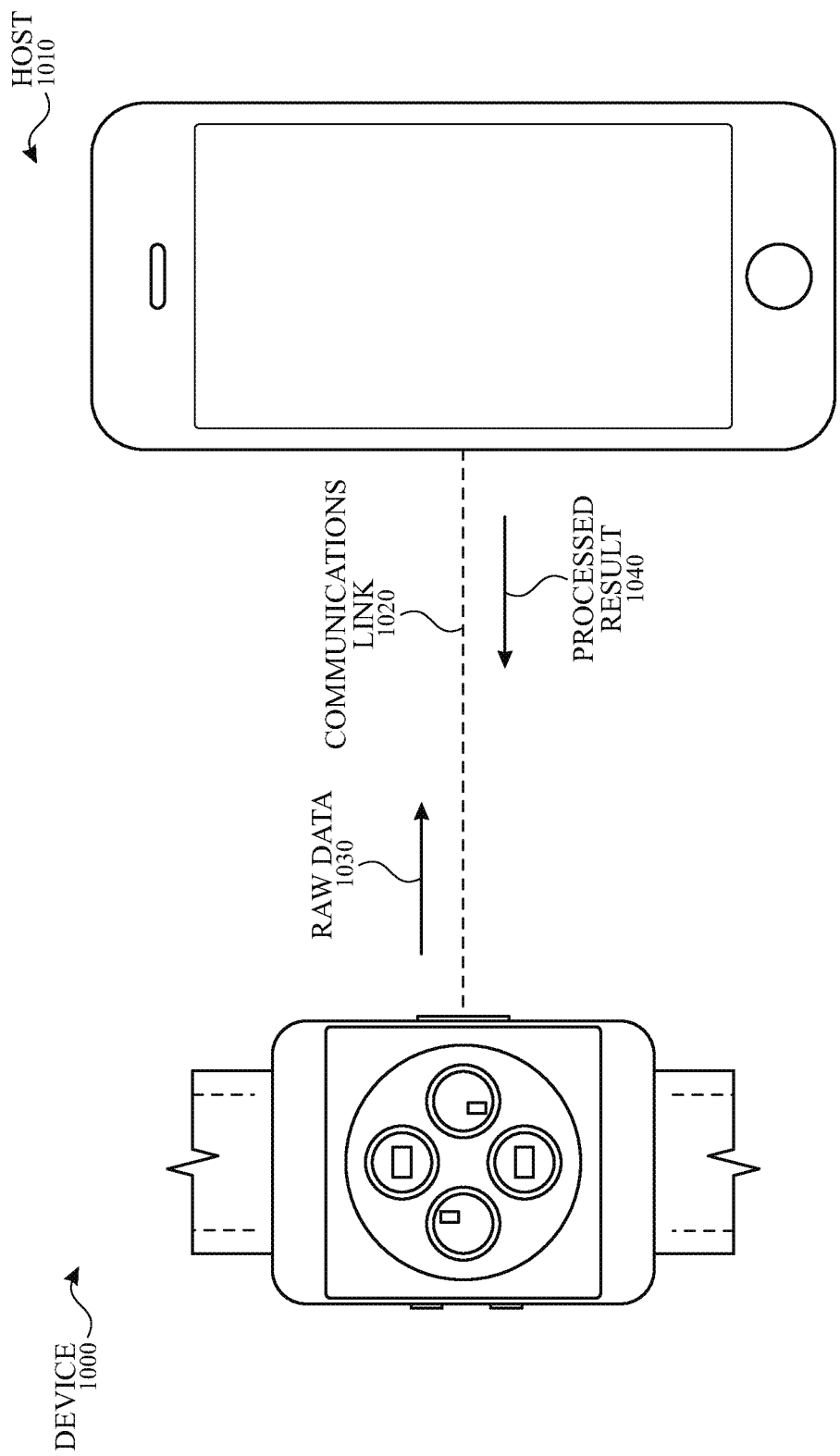
FIG. 10 illustrates an exemplary configuration in which an electronic device is connected to a host according to examples of the disclosure.

In some examples, the light sensors can measure light information and a processor can determine the physiological information from the reflected or absorbed light. Processing of the light information can be performed on the device as well. In some examples, processing of light information need not be performed on the device itself. FIG. 10 illustrates an exemplary configuration in which an electronic device is connected to a host according to examples of the disclosure. Host 1010 can be any device external to device 1000 including, but not limited to, any of the systems illustrated in FIGS. 1A-1C or a server. Device 1000 can be connected to host 1010 through communications link 1020. Communications link 1020 can be any connection including, but not limited to, a wireless connection and a wired connection. Exemplary wireless connections include Wi-Fi, Bluetooth, Wireless Direct and Infrared. Exemplary wired connections include Universal Serial Bus (USB), FireWire, Thunderbolt, or any connection requiring a physical cable.

In operation, instead of processing light information from the light sensors on the device 1000 itself, device 1000 can send raw data 1030 measured from the light sensors over communications link 1020 to host 1010. Host 1010 can receive raw data 1030, and host 1010 can process the light information. Processing the light information can include canceling or reducing any noise due to artifacts and determining physiological signals such as a user's heart rate. Host 1010 can include algorithms or calibration procedures to account for differences in a user's characteristics affecting the measured signals. Additionally, host 1010 can include storage or memory for tracking physiological information history for diagnostic purposes. Host 1010 can send the processed result 1040 or related information back to device 1000. Based on the processed result 1040, device 1000 can notify the user or adjust its operation accordingly. By offloading the processing and/or storage of the light information, device 1000 can conserve space and power-enabling device 1000 to remain small and portable, as space that could otherwise be required for processing logic can be freed up on the device.

In some examples, an optical layer is disclosed. The optical layer can comprise: an optical film including a plurality of regions, each region configured to allow light having an angle of incidence within a plurality of viewing angles to pass through, the plurality of viewing angles of each region different from the plurality of viewing angles of other regions, wherein each region is further configured to prevent light having an angle of incidence outside of the plurality of viewing angles from passing through. Additionally or alternatively, in some examples, the optical layer further comprises: a Fresnel lens, wherein the Fresnel lens and the optical film are a continuous layer. Additionally or alternatively, in some examples, the optical layer further comprises: an opaque mask, wherein the Fresnel lens, opaque mask, and optical film are a continuous layer. Additionally or alternatively, in some examples, the optical layer of claim 1, further comprises: a Fresnel lens disposed on the optical film. Additionally or alternatively, in some examples, the optical film includes: a plurality of accepting sections, each accepting section configured to allow the light to pass through, wherein each of the plurality of accepting sections has the same width as the other of the plurality of accepting sections; and a plurality of blocking sections, each block section configured to prevent light having an angle of incidence outside of the plurality of viewing angles from passing through. Additionally or alternatively, in some examples, the optical film includes: a plurality of accepting sections, each accepting section configured to allow the light to pass through; and a plurality of blocking sections, each block section configured to prevent light having an angle of incidence outside of the plurality of viewing angles from passing through, wherein at least two of the plurality of blocking sections have different heights. Additionally or alternatively, in some examples, the heights of the plurality of blocking sections gradually vary. Additionally or alternatively, in some examples, the optical film includes: a plurality of accepting sections, each accepting section configured to allow the light to pass through; and a plurality of blocking sections, each block section configured to prevent light having an angle of incidence outside of the plurality of viewing angles from passing through, wherein at least two of the plurality of blocking sections have different tilts. Additionally or alternatively, in some examples, the optical layer further comprising: a section configured to accept light having optical properties different from the optical film, wherein the section and the optical film are a continuous layer. Additionally or alternatively, in some examples, the section includes an infrared transparent material. Additionally or alternatively, in some examples, at least two of the regions are configured to allow light having different wavelengths to pass through. Additionally or alternatively, in some examples, one region is configured to allow visible light to pass through, and another region is configured to allow infrared light to pass through.

In some examples, an optical layer is disclosed. The optical layer can comprise: an optical film configured to: allow light from a first direction having an angle of incidence within a plurality of first viewing angles to pass through, prevent light from the first direction having an angle of incidence outside of the plurality of first viewing angles from passing through, allow light from a second direction, different from the first direction, having an angle of incidence within a plurality of second viewing angles, different from the first viewing angles, to pass through, and prevent light from the second direction having an angle of incidence outside of the plurality of second viewing angles from passing through. Additionally or alternatively, in some examples, the optical film includes: a plurality of accepting sections, each accepting section configured to allow the light to pass through, wherein each acceptance section includes an angled edge; and a plurality of blocking sections, each block section configured to prevent the light having an angle of incidence outside of the plurality of first and second viewing angles from passing through. Additionally or alternatively, in some examples, the optical layer of claim 13, further comprises: a Fresnel lens, wherein the Fresnel lens and the optical film are a continuous layer.

In some examples, a device is disclosed. The device can comprise: one or more light emitters configured to emit light; one or more light sensors configured to detect at a least a portion of the emitted light; one or more windows configured to allow light from the one or more light emitters, the one or more light sensors, or both to pass through, at least one window including an emitter region, a reception region, and a boundary region; and an optical layer disposed on the one or more windows, the optical layer comprising: an optical film including a plurality of regions, each region configured to allow light having an angle of incidence within a plurality of viewing angles to pass through, the plurality of viewing angles of each region different from the plurality of viewing angles of other regions, wherein each region is further configured to prevent light having an angle of incidence outside of the plurality of viewing angles from passing through, wherein the optical layer covers a portion of the reception region of the at least one window. Additionally or alternatively, in some examples, the device further comprises: an isolation located between at least one of the one or more light emitters and at least one of the one or more light sensors, wherein the isolation is further located in the boundary region of the at least one window, wherein the optical film covers the boundary region of the at least one window. Additionally or alternatively, in some examples, the plurality of accepting sections includes at least one first accepting section and at least one second accepting section, the first accepting section configured with one or more first acceptance angles and the second accepting section configured with one or more second acceptance angles, the one or more second acceptance angles including at least one wider viewing angle than the one or more first acceptance angles, and the at least first accepting section located closer to at least one of the one or more light emitters than the at least second accepting section.

In some examples, a method for determining one or more physiological information of a user is disclosed. The method can comprise: emitting light from one or more light emitters; transmitting the emitted light through one or more windows; allowing at least a portion of the emitted light to transmit through an optical layer including: allowing a portion of the emitted light having an angle of incidence within first viewing angles at a first region of the optical layer, allowing a portion of the emitted light having an angle of incidence within second viewing angles, different from the first viewing angles, at a second region, different from the first region, of the optical layer, and blocking a portion of the emitted light having an angle of incidence outside of the first and second viewing angles; detecting the allowed portion of the emitted light by one or more light sensors; and determining the one or more physiological information from the detected allowed portion of the emitted light.

In some examples, a method for determining one or more physiological information of a user is disclosed. The method can comprise: emitting light from one or more light emitters; transmitting the emitted light through one or more windows; allowing at least a portion of the emitted light to transmit through an optical layer including: allowing a portion of the emitted light from a first direction and having an angle of incidence within first viewing angles, allowing a portion of the emitted light from a second direction, different from the first direction, having an angle of incidence within second viewing angles, different from the first viewing angles, at a second region, different from the first region, of the optical layer, and blocking a portion of the emitted light having an angle of incidence outside of the first and second viewing angles; detecting the allowed portion of the emitted light by one or more light sensors; and determining the one or more physiological information from the detected allowed portion of the emitted light.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:
1. An optical layer comprising:
   an optical film including a plurality of sections, each section configured to allow light having an angle of incidence within a plurality of viewing angles to pass through, the plurality of viewing angles of each section different from the plurality of viewing angles of other section,
   wherein each section is further configured to prevent light having an angle of incidence outside of the plurality of viewing angles from passing through; and a Fresnel lens, wherein the Fresnel lens and the optical film are positioned side by side in a continuous layer.

2. The optical layer of claim 1, further comprising:
an opaque mask, wherein the Fresnel lens, the opaque mask, and the optical film are a continuous layer.

3. The optical layer of claim 1, wherein the optical film includes:
a plurality of accepting sections of the plurality of sections, each accepting section configured to allow the light to pass through, wherein each of the plurality of accepting sections has the same width as other of the plurality of accepting sections; and
a plurality of blocking sections, each blocking section configured to prevent light having an angle of incidence outside of the plurality of viewing angles from passing through.

4. The optical layer of claim 1, wherein the optical film includes:
a plurality of accepting sections of the plurality of sections, each accepting section configured to allow the light to pass through; and
a plurality of blocking sections, each blocking section configured to prevent light having an angle of incidence outside of the plurality of viewing angles from passing through, wherein at least two of the plurality of blocking have different heights.

5. The optical layer of claim 4, wherein the heights of the plurality of blocking sections vary gradually.

6. The optical layer of claim 1, wherein the optical film includes:
a plurality of accepting sections, each accepting section configured to allow the light to pass through; and
a plurality of blocking sections, each blocking section configured to prevent light having an angle of incidence outside of the plurality of viewing angles from passing through, wherein at least two of the plurality of blocking sections have different tilts.

7. The optical layer of claim 1, further comprising:
an additional section configured to accept light, the additional section having optical properties different from the optical film, wherein the additional section and the optical film are a continuous layer.

8. The optical layer of claim 7, wherein the section includes an infrared transparent material.

9. The optical layer of claim 1, wherein at least two of the sections are configured to allow light having different wavelengths to pass through.

10. The optical layer of claim 9, wherein one section is configured to allow visible light to pass through, and another section is configured to allow infrared light to pass through.

11. The optical layer of claim 1, wherein the plurality of sections are further configured to:
allow light from a first direction having an angle of incidence within a plurality of first viewing angles to pass through,
prevent light from the first direction having an angle of incidence outside of the plurality of first viewing angles from passing through,
allow light from a second direction, different from the first direction, having an angle of incidence within a plurality of second viewing angles, different from the first viewing angles, to pass through, and
prevent light from the second direction having an angle of incidence outside of the plurality of second viewing angles from passing through.

12. The optical layer of claim 11, wherein the optical film includes:
a plurality of accepting sections, each accepting section configured to allow the light to pass through, wherein each accepting section includes an angled edge; and
a plurality of blocking sections, each blocking section configured to prevent the light having an angle of incidence outside of the plurality of first and second viewing angles from passing through.

13. A device comprising:
one or more light emitters configured to emit light;
one or more light sensors configured to detect at a least a portion of the emitted light;
one or more windows configured to allow light from the one or more light emitters, the one or more light sensors, or both to pass through,
at least one window including an emitter region, a reception region, and a boundary region; and
an optical layer disposed on the one or more windows, the optical layer comprising:
an optical film including a plurality of sections, each section configured to allow light having an angle of incidence within a plurality of viewing angles to pass through, the plurality of viewing angles of each section different from the plurality of viewing angles of other sections; and
a Fresnel lens, wherein the Fresnel lens and the optical film are positioned side by side in a continuous layer,
wherein each section is further configured to prevent light having an angle of incidence outside of the plurality of viewing angles from passing through,
wherein the optical layer covers a portion of the reception region of the at least one window.

14. The device of claim 13, further comprising:
an isolation located between at least one of the one or more light emitters and at least one of the one or more light sensors,
wherein the isolation is further located in the boundary region of the at least one window,
wherein the optical film covers the boundary region of the at least one window.

15. The device of claim 14, wherein the optical film further comprises a plurality of accepting sections includes at least one first accepting section and at least one second accepting section, the first accepting section configured with one or more first acceptance angles and the second accepting section configured with one or more second acceptance angles, the one or more second acceptance angles including at least one wider viewing angle than the one or more first acceptance angles, and the at least first accepting section located closer to at least one of the one or more light emitters than the at least second accepting section.

16. A method for determining one or more physiological information of a user, the method comprising:
emitting light from one or more light emitters;
transmitting the emitted light through one or more windows;
allowing at least a portion of the emitted light to transmit through an optical layer, wherein the optical layer includes an optical film and a Fresnel lens positioned side by side in a continuous layer, and allowing at least a portion of the emitted light to transmit through an optical layer includes:
allowing a portion of the emitted light having an angle of incidence within first viewing angles at a first section of the optical layer, allowing a portion of the emitted light having an angle of incidence within second viewing angles, different from the first viewing angles, at a second section, different from the first section, of the optical layer, and blocking a portion of the emitted light having an angle of incidence outside of the first and second viewing angles;

detecting the allowed portion of the emitted light by one or more light sensors; and determining the one or more physiological information from the detected allowed portion of the emitted light.

17. The method of claim 16, wherein the allowance of at least the portion of the emitted light further comprises:

allowing a portion of the emitted light from a first direction and having the angle of incidence within the first viewing angles at the first section of the optical layer; and allowing a portion of the emitted light from a second direction, different from the first direction, having the angle of incidence within the second viewing angles at the second section of the optical layer.

* * * * *